US011141225B2

(12) United States Patent
Yi

(10) Patent No.: US 11,141,225 B2
(45) Date of Patent: Oct. 12, 2021

(54) IMAGE MATCHING DEVICE AND IMAGE MATCHING METHOD

(71) Applicants: KOH YOUNG TECHNOLOGY INC., Seoul (KR); INDUSTRY-UNIVERSITY COOPERATION FOUNDATION HANYANG UNIVERSITY ERICA CAMPUS, Ansan-si (KR)

(72) Inventor: Byung Ju Yi, Bucheon-si (KR)

(73) Assignees: KOH YOUNG TECHNOLOGY INC., Seoul (KR); INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 216 days.

(21) Appl. No.: 16/487,303

(22) PCT Filed: Feb. 21, 2018

(86) PCT No.: PCT/KR2018/002111
§ 371 (c)(1),
(2) Date: Aug. 20, 2019

(87) PCT Pub. No.: WO2018/155894
PCT Pub. Date: Aug. 30, 2018

(65) Prior Publication Data
US 2020/0015911 A1    Jan. 16, 2020

Related U.S. Application Data

(60) Provisional application No. 62/461,507, filed on Feb. 21, 2017.

(51) Int. Cl.
*A61B 5/00*    (2006.01)
*A61B 34/20*    (2016.01)
(Continued)

(52) U.S. Cl.
CPC .............. *A61B 34/20* (2016.02); *A61B 5/0077* (2013.01); *A61B 6/032* (2013.01); *A61B 90/361* (2016.02);
(Continued)

(58) Field of Classification Search
CPC ..... A61B 34/20; A61B 90/361; A61B 5/0077; A61B 6/032; A61B 2034/2055;
(Continued)

(56) References Cited

U.S. PATENT DOCUMENTS 7,894,649 B2    2/2011  Fu et al.
2001/0026637 A1  10/2001  Lelong et al.
(Continued)

FOREIGN PATENT DOCUMENTS

JP    2006-508719    3/2006
JP    2016-093497    5/2016
(Continued)

OTHER PUBLICATIONS

International Search Report with English translation for International Application No. PCT/KR2018/002111, dated Jun. 11, 2018.
(Continued)

*Primary Examiner* — Joel Lamprecht
(74) *Attorney, Agent, or Firm* — Kile Park Reed & Houtteman PLLC

(57) ABSTRACT

The present disclosure provides an image matching device. The image matching device according to the present disclosure includes a 3D scanner configured to three-dimensionally scan a dorsal surface of a patient to obtain a first dorsal surface scan image, a tracking sensor configured to obtain position and posture information of a reference marker and position and posture information of a scanner marker, and a processor configured to generate a virtual first vertebrae measurement image for estimation of a position of the
(Continued)

vertebrae of the patient based on a human body correlation model and the first dorsal surface scan image and match a coordinate system of the virtual first vertebrae measurement image with a coordinate system of the patient based on the position and posture information of the reference marker and the position and posture information of the scanner marker.

20 Claims, 9 Drawing Sheets

(51) Int. Cl.
  *A61B 90/00* (2016.01)
  *A61B 6/03* (2006.01)
(52) U.S. Cl.
  CPC ............... *A61B 2034/2055* (2016.02); *A61B 2034/2065* (2016.02); *A61B 2034/2072* (2016.02)
(58) Field of Classification Search
  CPC .... A61B 2034/2065; A61B 2034/2072; A61B 2034/256; A61B 2090/364; A61B 34/10; A61B 2034/105; A61B 5/00; A61B 5/055; A61B 6/03; A61B 90/00; A61B 5/0062; A61B 90/39; G06T 7/344
  See application file for complete search history.

(56) References Cited

U.S. PATENT DOCUMENTS

| | | |
|---|---|---|
| 2003/0130576 A1 | 7/2003 | Seeley et al. |
| 2004/0106861 A1 | 6/2004 | Leitner |
| 2006/0282023 A1 | 12/2006 | Leitner |
| 2013/0034203 A1 | 2/2013 | Wang et al. |
| 2013/0060146 A1 | 3/2013 | Yang et al. |
| 2016/0030131 A1 | 2/2016 | Yang et al. |
| 2017/0042622 A1 | 2/2017 | Yang et al. |
| 2018/0153626 A1 | 6/2018 | Yang et al. |

FOREIGN PATENT DOCUMENTS

| | | |
|---|---|---|
| JP | 6063599 | 1/2017 |
| KR | 10-2013-0104097 | 9/2013 |
| WO | 2011/134083 | 11/2011 |

OTHER PUBLICATIONS

Written Opinion with English translation for International Application No. PCT/KR2018/002111, dated Jun. 11, 2018.
Japanese Office Action, with English translation, corresponding to Japanese Application No. 2019-566557, dated Oct. 27, 2020.
Extended European search report, corresponding to European Application No./ Patent No. 18758278.8, dated Feb. 7, 2020.
India Office Action, with English translation, corresponding to Indian Application No. 201917036930, dated Jun. 24, 2021.

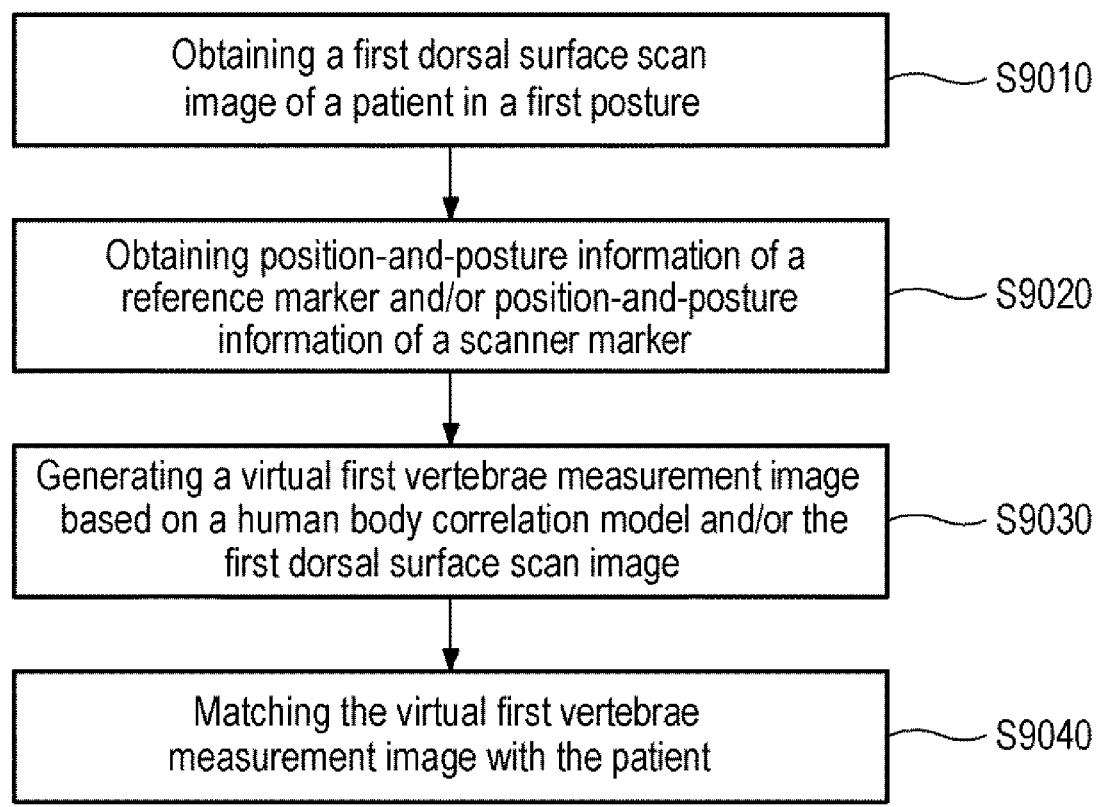

IMAGE MATCHING DEVICE AND IMAGE MATCHING METHOD

This application is based upon and claims the benefit of priority from U.S. Provisional Patent Application No. 62/461,507, filed on Feb. 21, 2017, the entire contents of which are incorporated herein by reference.

TECHNICAL FIELD

The present disclosure relates to an image matching device and an image matching method.

The present disclosure is derived from a study conducted as part of the technical development support of the WC300 project of the Korean Ministry of SMEs and Startups.

[Project No.: S2482672, Project Title: Development of head/neck surgery robot system for surgery with matching accuracy of less than 1 mm combined with surgical navigation]

BACKGROUND

In operating on a vertebrae of a patient, image-guided surgery using the captured images of a patient's affected area has been widely used. In particular, when there is a need to perform surgery while avoiding important nerves and major organs in the patient's body, it is required to perform surgery with high accuracy based on the captured images.

In addition, minimal invasive surgery (MIS) has been utilized as it becomes possible to obtain high resolution images from the body of a patient and as it becomes possible to finely manipulate a medical instrument using a robot arm or the like. That is, a small hole may be formed in the skin without directly making an incision in the human body, and a surgical tool such as a medical needle or the like may be put into the hole to perform surgery. In such a minimal invasive surgery, it is common to use the above-described image-guided surgery together so that a user such as a doctor or the like performs surgery while observing the inside of the human body through the use of images.

In the minimal invasive surgery using images, it is necessary to continuously or intermittently capture images of a patient during surgery using a video diagnosis device or the like. This is because, when performing vertebrae surgery, it is required to locate the vertebrae with high accuracy. In particular, under a situation where the incision is minimized, the capture of images of a patient is inevitable in order to accurately locate the vertebrae to be subjected to surgery.

To this end, vertebrae surgery is performed while capturing images through the use of a C-arm type or O-arm type imaging device. However, this method has a problem that the patient is exposed to a large amount of X-rays. In addition, this method has a problem of increasing the cost of surgery for the patient because the capture of images is simultaneously performed.

The vertebrae surgery may be performed based on the existing vertebrae images captured by a patient before the surgery. However, in this case, the accuracy of estimation of a vertebrae position is significantly reduced. In particular, since the posture at the time of surgery of the patient is different from the posture when the vertebrae images are captured before surgery, it may be difficult to accurately find the vertebrae to be subjected to surgery.

SUMMARY

Various embodiments of the present disclosure provide an image matching device and an image matching method for solving the problems of the related art set forth above.

According to one embodiment of the present disclosure, there is provided an image matching device, including: a 3D scanner configured to three-dimensionally scan a dorsal surface of a patient supported on a surgery table in a first posture to obtain a first dorsal surface scan image; a tracking sensor configured to obtain position and posture information of a reference marker provided on a body of the patient and position and posture information of a scanner marker provided on the 3D scanner; a memory configured to store a human body correlation model on a correlation between the dorsal surface and a vertebrae of the patient; and a processor electrically connected to the 3D scanner, the tracking sensor and the memory, wherein the processor generates a virtual first vertebrae measurement image for estimation of a position of the vertebrae of the patient based the human body correlation model and the first dorsal surface scan image and matches a coordinate system of the virtual first vertebrae measurement image with a coordinate system of the patient based on the position and posture information of the reference marker and the position and posture information of the scanner marker.

In one embodiment, the processor may extract dorsal surface information of the patient in the first posture from the first dorsal surface scan image, may obtain vertebrae position information of the patient in the first posture based on the human body correlation model and the dorsal surface information, and may generate the virtual first vertebrae measurement image based on the vertebrae position information.

In one embodiment, the human body correlation model may be a first correlation model that is generated by using a correlation between a second dorsal surface scan image obtained by three-dimensionally scanning the dorsal surface of the patient in a second posture and a second vertebrae measurement image obtained by capturing an image of the vertebrae of the patient in the second posture.

In one embodiment, the human body correlation model may be a second correlation model that is generated by correcting the first correlation model using a correlation between a third dorsal surface scan image obtained by three-dimensionally scanning the dorsal surface of at least one patient selected from a group of different patients and a third vertebrae measurement image obtained by capturing an image of a vertebrae of the at least one patient.

In one embodiment, the device may further include: a vertebrae image camera configured to capture an image of the vertebrae of the patient in the first posture to obtain a fourth vertebrae measurement image, wherein the processor may be further configured to correct the human body correlation model using a correlation between the fourth vertebrae measurement image and the first dorsal surface scan image and to generate the virtual first vertebrae measurement image using the corrected human body correlation model.

In one embodiment, the processor may be further configured to repeatedly perform, a predetermined number of times, the correction of the human body correlation model based on the fourth vertebrae measurement image.

In one embodiment, the device may further include: a robot arm having a distal end to which a surgical tool is attached, wherein the tracking sensor may obtain position and posture information of a robot arm marker provided on the robot arm, and the processor may control the robot arm based on the position and posture information of the robot arm marker appearing on the coordinate system of the patient matched with the coordinate system of the virtual first vertebrae measurement image.

In one embodiment, the processor may be further configured to obtain a third coordinate transformation relationship between the virtual first vertebrae measurement image and the position and posture information of the reference marker, based on the position and posture information of the reference marker, the position and posture information of the scanner marker, a first coordinate transformation relationship between the position and posture information of the scanner marker and the first dorsal surface scan image and a second coordinate transformation relationship between the first dorsal surface scan image and the virtual first vertebrae measurement image, and to match the coordinate system of the virtual first vertebrae measurement image with the coordinate system of the patient based on the third coordinate transformation relationship.

In one embodiment, each of the second vertebrae measurement image, the third vertebrae measurement image and the fourth vertebrae measurement image may be one of a Computed Tomography Angiograph (CTA) image, a Magnetic Resonance Imaging (MRI) image and a Computed Tomography (CT) image.

According to one embodiment of the present disclosure, there is provided an image matching method, including: obtaining, by a 3D scanner, a first dorsal surface scan image by three-dimensionally scanning a dorsal surface of a patient supported on a surgery table in a first posture; obtaining position and posture information of a reference marker provided on a body of the patient and position and posture information of a scanner marker provided on the 3D scanner; generating a virtual first vertebrae measurement image for estimation of a position of a vertebrae of the patient based a human body correlation model on a correlation between the dorsal surface and the vertebrae of the patient and the first dorsal surface scan image; and matching a coordinate system of the virtual first vertebrae measurement image with a coordinate system of the patient based on the position and posture information of the reference marker and the position and posture information of the scanner marker.

In one embodiment, the generating the virtual first vertebrae measurement image may include: extracting dorsal surface information of the patient in the first posture from the first dorsal surface scan image; obtaining vertebrae position information of the patient in the first posture based on the human body correlation model and the dorsal surface information; and generating the virtual first vertebrae measurement image based on the vertebrae position information.

In one embodiment, the method may further include: obtaining a fourth vertebrae measurement image by capturing an image of the vertebrae of the patient in the first posture; and correcting the human body correlation model using a correlation between the fourth vertebrae measurement image and the first dorsal surface scan image, wherein the generating the virtual first vertebrae measurement image may include generating the virtual first vertebrae measurement image using the corrected human body correlation model.

In one embodiment, the correcting the human body correlation model may be repeatedly performed a predetermined number of times.

In one embodiment, the method may further include: obtaining position and posture information of a robot arm marker provided on a robot arm having a distal end to which a surgical tool is attached; and controlling the robot arm based on the position and posture information of the robot arm marker appearing on the coordinate system of the patient matched with the coordinate system of the virtual first vertebrae measurement image.

In one embodiment, the matching the coordinate system of the virtual first vertebrae measurement image with the coordinate system of the patient may include: obtaining a third coordinate transformation relationship between the virtual first vertebrae measurement image and the position and posture information of the reference marker, based on the position and posture information of the reference marker, the position and posture information of the scanner marker, a first coordinate transformation relationship between the position and posture information of the scanner marker and the first dorsal surface scan image and a second coordinate transformation relationship between the first dorsal surface scan image and the virtual first vertebrae measurement image; and matching the coordinate system of the virtual first vertebrae measurement image with the coordinate system of the patient based on the third coordinate transformation relationship.

According to one embodiment of the present disclosure, there is provided a non-transitory computer-readable recording medium storing a program to be executed on a computer, the program including executable commands for, when executed by a processor, causing the processor to perform: obtaining a first dorsal surface scan image by causing a 3D scanner to three-dimensionally scan a dorsal surface of a patient supported on a surgery table in a first posture; obtaining position and posture information of a reference marker provided on a body of the patient and position and posture information of a scanner marker provided on the 3D scanner; generating a virtual first vertebrae measurement image for estimation of a position of a vertebrae of the patient based a human body correlation model on a correlation between the dorsal surface and the vertebrae of the patient and the first dorsal surface scan image; and matching a coordinate system of the virtual first vertebrae measurement image with a coordinate system of the patient based on the position and posture information of the reference marker and the position and posture information of the scanner marker.

According to the image matching device and the image matching method of the embodiment, it is possible to reduce the X-ray exposure during surgery of a patient to be subjected to surgery.

In addition, since the capturing of images using a C-arm or the like is minimized during surgery, it is possible to reduce the surgery cost.

In addition, since the position of the vertebrae of a patient is estimated using the human body correlation model, it is possible to deal with a change in the posture of the patient during surgery, thereby increasing the accuracy of surgery.

BRIEF DESCRIPTION OF DRAWINGS

FIG. 9 is a diagram showing an image matching method that may be implemented by the image matching device according to an embodiment of the present disclosure.

DETAILED DESCRIPTION

Figure 1:
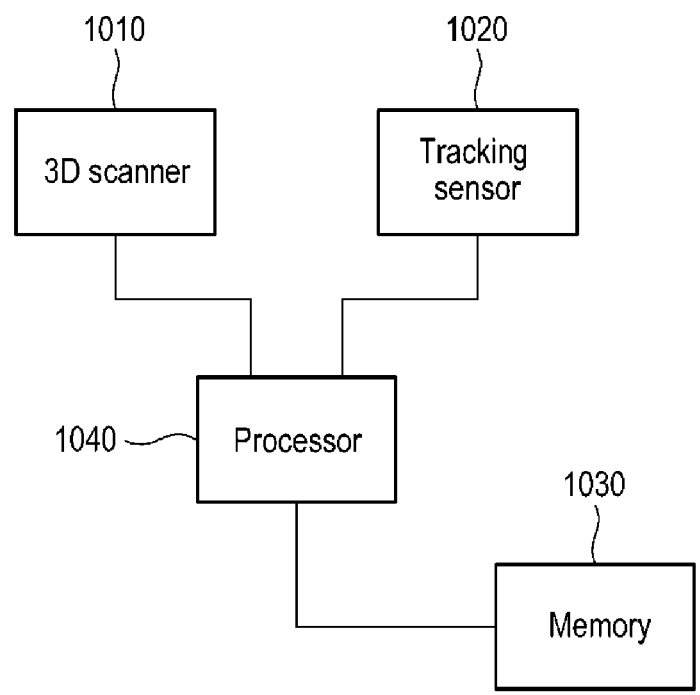
FIG. 1 is a diagram showing an image matching device according to an embodiment of the present disclosure.

Embodiments of the present disclosure are illustrated for describing the technical spirit of the present disclosure. The scope of the claims according to the present disclosure is not limited to the embodiments described below or to the detailed descriptions of these embodiments.

All technical or scientific terms used herein have meanings that are generally understood by a person having ordinary knowledge in the art to which the present disclosure pertains, unless otherwise specified. The terms used herein are selected merely for more clear illustration of the present disclosure, and are not intended to limit the scope of the claims in accordance with the present disclosure.

The expressions "include", "provided with", "have" and the like used herein should be understood as open-ended terms connoting the possibility of inclusion of other embodiments, unless otherwise mentioned in a phrase or sentence including the expressions.

A singular expression can include meanings of plurality, unless otherwise mentioned, and the same is applicable to a singular expression stated in the claims.

The terms "first", "second", etc. used herein are used to identify a plurality of components from one another, and are not intended to limit the order or importance of the relevant components.

The term "unit" used in these embodiments means a software component or hardware component, such as a field-programmable gate array (FPGA) and an application specific integrated circuit (ASIC). However, a "unit" is not limited to software and hardware, it may be configured to be an addressable storage medium or may be configured to run on one or more processors. For example, a "unit" may include components, such as software components, object-oriented software components, class components, and task components, as well as processors, functions, attributes, procedures, subroutines, segments of program codes, drivers, firmware, micro-codes, circuits, data, databases, data structures, tables, arrays, and variables. Functions provided in components and "unit" may be combined into a smaller number of components and "units" or further subdivided into additional components and "units."

The expression "based on" used herein is used to describe one or more factors that influence a decision, an action of judgment or an operation described in a phrase or sentence including the relevant expression, and this expression does not exclude additional factor influencing the decision, the action of judgment or the operation.

When a certain component is described as "coupled to" or "connected to" another component, this should be understood as having the meaning that the certain component may be coupled or connected directly to the other component or that the certain component may be coupled or connected to the other component via a new intervening component.

Hereinafter, embodiments of the present disclosure will be described with reference to the accompanying drawings. In the accompanying drawings, like or relevant components are indicated by like reference numerals. In the following description of embodiments, repeated descriptions of the identical or relevant components will be omitted. However, even if a description of a component is omitted, such a component is not intended to be excluded in an embodiment.

FIG. 1 is a diagram showing an image matching device according to an embodiment of the present disclosure.

According to an embodiment, the present disclosure may be related to an image matching device. The image matching device may generate a virtual vertebrae measurement image for the vertebrae of a patient from a dorsal surface scan image of the patient using the correlation between the dorsal surface and the vertebrae. In addition, the image matching device may match the generated virtual vertebrae measurement image with the body of the patient.

Specifically, the image matching device may three-dimensionally scan a dorsal surface of a patient supported on a surgery table to obtain a dorsal surface scan image, may generate a virtual vertebrae measurement image based on a human body correlation model, which indicates a correlation between the dorsal surface and the vertebrae, and/or the dorsal surface scan image, may obtain position and posture information of a reference marker provided on a body of a patient and a scanner marker provided on a 3D scanner, and may match the virtual vertebrae measurement image with the body of the patient.

The image matching device according to the present disclosure may include a 3D scanner 1010, a tracking sensor 1020, a memory 1030, and/or a processor 1040 as internal/external components.

The 3D scanner 1010 may three-dimensionally scan the dorsal surface of the patient in an intra-operative posture from the patient supported on the surgery table. The 3D scanner 1010 may obtain a dorsal surface scan image of the patient in the intra-operative posture. The 3D scanner 1010 may transmit the obtained dorsal surface scan image to the processor 1040. The dorsal surface scan image obtained in this process may be referred to as a first dorsal surface scan image in some embodiments.

In this regard, the scan image obtained by the 3D scanner may be 3D information which can be represented by three-dimensionally scanning the surface of an object. That is, the dorsal surface scan image may be a 3D dorsal surface scan image obtained by three-dimensionally scanning the dorsal surface. In addition, the dorsal surface shape information obtained from the dorsal surface scan image may be 3D dorsal surface shape information which three-dimensionally represents the dorsal surface shape.

The tracking sensor 1020 may sense markers to obtain position and posture information of the markers. In some embodiments, the tracking sensor 1020 may obtain position and posture information of markers from a reference marker and/or a scanner marker. The reference marker may be a marker provided on the body of the patient, and the scanner marker may be a marker provided on the 3D scanner 1010. As used herein, the expression "a marker is provided on a specific object" may mean that the marker is fixedly installed on or attached to the specific object. The tracking sensor 1020 may transmit the obtained position and posture information of the markers to the processor 1040.

The memory 1030 may store a human body correlation model indicating a correlation between the dorsal surface and the vertebrae. Details of the human body correlation model will be described later.

The processor 1040 may generate a virtual vertebrae measurement image based on the dorsal surface scan image of the patient in the intra-operative posture obtained by the 3D scanner 1010 and the human body correlation model stored in the memory. The virtual vertebrae measurement image may be a virtual vertebrae image for estimating the position of the vertebrae of the patient in the intra-operative posture. The virtual vertebrae measurement image generated in this process may be referred to as a virtual first vertebrae measurement image in some embodiments.

In addition, the processor 1040 may match the virtual vertebrae measurement image with the body of the patient based on the position and posture information of the markers. Specifically, the processor 1040 may match the coordinate system of the virtual vertebrae measurement image with the coordinate system of the patient based on the position and posture information of the reference marker and/or the position and posture information of the scanner marker obtained by the tracking sensor 1020.

The processor 1040 may be electrically connected to the 3D scanner 1010, the tracking sensor 1020 and/or the memory 1030.

In one embodiment, the processor 1040 may extract the dorsal surface information of the patient in the intra-operative posture from the dorsal surface scan image obtained from the patient supported on the surgery table. The processor 1040 may obtain the vertebrae position information of the patient in the intra-operative posture based on the human body correlation model and the extracted dorsal surface information. The processor 1040 may generate the virtual vertebrae measurement image based on the obtained vertebrae position information.

In one embodiment, the human body correlation model may be a human body model representing the correlation between the dorsal surface and the vertebrae. The human body correlation model may be a human body correlation model indicating the correlation between the shape of the dorsal surface and the vertebrae position in the human body corresponding to the shape of the dorsal surface.

In one embodiment, the human body correlation model may be a patient-specific human body correlation model for the patient. The patient-specific human body correlation model may be a human body correlation model in accordance with the correlation between the dorsal surface and the vertebrae for the individual patient, which takes the characteristics of the patient into consideration. The human body correlation model generated in this process may be referred to as a first correlation model. Details of the patient-specific correlation model will be described later.

In one embodiment, the human body correlation model may be a database-based human body correlation model. The database-based human body correlation model may be a human body correlation model obtained by correcting the aforementioned patient-specific human body correlation model using information on the dorsal surface and/or the vertebrae of at least one or more patients stored in the database. The human body correlation model generated in this process may be referred to as a second correlation model. Details of the database-based human body correlation model will be described later.

In one embodiment, the processor 1040 may further correct the aforementioned human body correlation model based on the additional information obtained from the intra-operative posture of the patient supported on the surgery table. The processor 1040 may generate the aforementioned virtual vertebrae measurement image by using the corrected human body correlation model.

In one embodiment, the image matching device may further include a vertebrae image camera (not shown). The vertebrae image camera may obtain a vertebrae measurement image in an intra-operative posture by capturing an image of the vertebrae of the patient supported on the surgery table. The dorsal surface scan image obtained in this process may be referred to as a fourth dorsal surface scan image in some embodiments. When correcting the human body correlation model based on the additional information obtained from the intra-operative posture of the patient as described above, the processor 1040 may use the correlation between the vertebrae measurement image obtained from the vertebrae image camera and the dorsal surface scan image (first dorsal surface scan image) in the aforementioned intra-operative posture.

In one embodiment, the processor 1040 may repeatedly perform, a predetermined number of times, the correction of the human body correlation model based on the additional information obtained from the intra-operative posture.

In one embodiment, the processor 1040 may obtain a coordinate transformation relationship between the generated virtual vertebrae measurement image and the position and posture information of the reference marker fixed to the body of the patient, and may match the coordinate system of the virtual vertebrae measurement image with the coordinate system of the patient based on the obtained coordinate transformation relationship.

In one embodiment, the marker tracked by the tracking sensor 1020 may be a reference body used to measure the motion or posture of an object. Specifically, the marker may be attached to an object. By measuring the positional information of the marker in a three-dimensional space and the posture information defined as roll, pitch and yaw, the tracking sensor 1020 may measure the current motion or posture of the object to which the marker is attached, or may track the motion or posture of the object that changes over time.

In one embodiment, the posture information of the marker may be expressed through the concept of the aircraft's principal axes, i.e., roll, pitch and yaw, in a three-dimensional space. In this regard, the roll, pitch and yaw may refer to axes, or directions, of rotation of the marker in a three-dimensional space. Roll may refer to an axis extending from the front part to the rear part of the object or the direction of rotation about the axis. Pitch may refer to a direction of up and down rotation with respect to the front part of the object or an axis of such rotation. Yaw may refer to a direction of left and right rotation with respect to the front part of the object or an axis of such rotation.

In one embodiment, a marker containing image information may be used to simultaneously measure the position and posture of the object to which the marker is attached. In some embodiments, the marker may contain image information formed through a printing technique, a stencil technique, a stamping technique or a lithography technique. Two or more arbitrary feature point coordinates corresponding to each other may be detected from an image formed by actually capturing the image contained in the marker and the information on the image stored in advance. The posture of the marker containing the corresponding image may be determined from the relation between the corresponding feature point coordinates. In addition, the image contained in the marker may be captured at a plurality of positions, and the position of the corresponding marker may be determined through trigonometry based on the information of the captured respective images.

In one embodiment, three or more markers may be used to simultaneously measure the position and posture of the object to which the markers are attached. The position of 6 degrees of freedom and the posture of the object may be measured using the respective markers.

In one embodiment, the reference marker may be a marker that serves as a reference for matching the virtual vertebrae measurement image with the body of the patient. In some embodiments, the reference marker may be fixed to the body of the patient. For example, the reference marker may be fixed to one of the vertebral bones of the patient, or a template having the reference marker may be fixed to the patient's teeth. Based on the position and posture information of the reference marker, the coordinate system of the virtual vertebrae measurement image may be matched with the coordinate system of the patient.

In one embodiment, the scanner marker may be a marker attached to the aforementioned 3D scanner and used to obtain a scanning point of the 3D scanner. A coordinate transformation relationship between a predetermined portion of the dorsal surface to be scanned by the 3D scanner and a dorsal surface scan image may be obtained based on the position and posture information of the scanner marker.

In one embodiment, the vertebrae measurement images except for the virtual vertebrae measurement image generated by the processor may be Computed Tomography Angiography (CTA) images, Magnetic Resonance Imaging (MRI) images, or Computed Tomography (CT) images. As used herein, the term "image" may mean an image obtained by capturing an internal structure of an object. Specifically, the image may be obtained by imaging and processing structural details, internal tissues and/or fluid flows in the body for minimal invasive inspection.

In one embodiment, the 3D scanner 1010, the tracking sensor 1020 and/or the vertebrae image camera may transmit the dorsal surface scan images, the position and posture information of the markers and/or the vertebrae measurement images to the memory 1030. The memory 1030 may store the dorsal surface scan images, the position and posture information of the markers and/or the vertebrae measurement images for future use.

In one embodiment, the image matching device may further include a network interface (not shown). The network interface may communicate with a server via broadband to receive the human body correlation model.

In one embodiment, the processor 1040 may directly generate the aforementioned human body correlation model. The processor 1040 may obtain the dorsal surface scan images and/or the vertebrae measurement images for the patient to be subjected to surgery from the memory 1030, and may generate a patient-specific human body correlation model for the patient. In some embodiments, the processor 1040 may obtain, from the memory 1030, the dorsal surface scan images and/or the vertebrae measurement images for at least one patient selected from a group of different patients, and may generate a database-based human body correlation model. In some embodiments, the processor 1040 may generate a patient-specific human body correlation model or a database-based human body correlation model using the dorsal surface scan images and/or the vertebrae measurement images obtained from the server through the network interface.

In one embodiment, the image matching device may further include a display (not shown). The display may display the back surface scan image of the patient in the intra-operative posture obtained by the 3D scanner 1010, the generated virtual vertebrae measurement image and/or the virtual vertebrae measurement image matched with the coordinate system of the patient.

In one embodiment, the image matching device may further include a robot arm, and the processor 1040 may control the robot arm.

In one embodiment, the image matching device may be defined as a device including only the above-described processor 1040 and the above-described memory 1030. In this embodiment, the image matching device may receive information from a 3D scanner, a tracking sensor and/or a vertebrae image camera which are provided outside the image matching device. The processor may perform the operations according to the above-described embodiments of the image matching device using the received information.

The above-described embodiments of the image matching device according to the present disclosure may be combined with each other. Furthermore, the internal/external components of the image matching device according to the present disclosure may be added, changed, replaced or deleted in some embodiments. In addition, the internal/external components of the image matching device may be realized by hardware.

Figure 2:
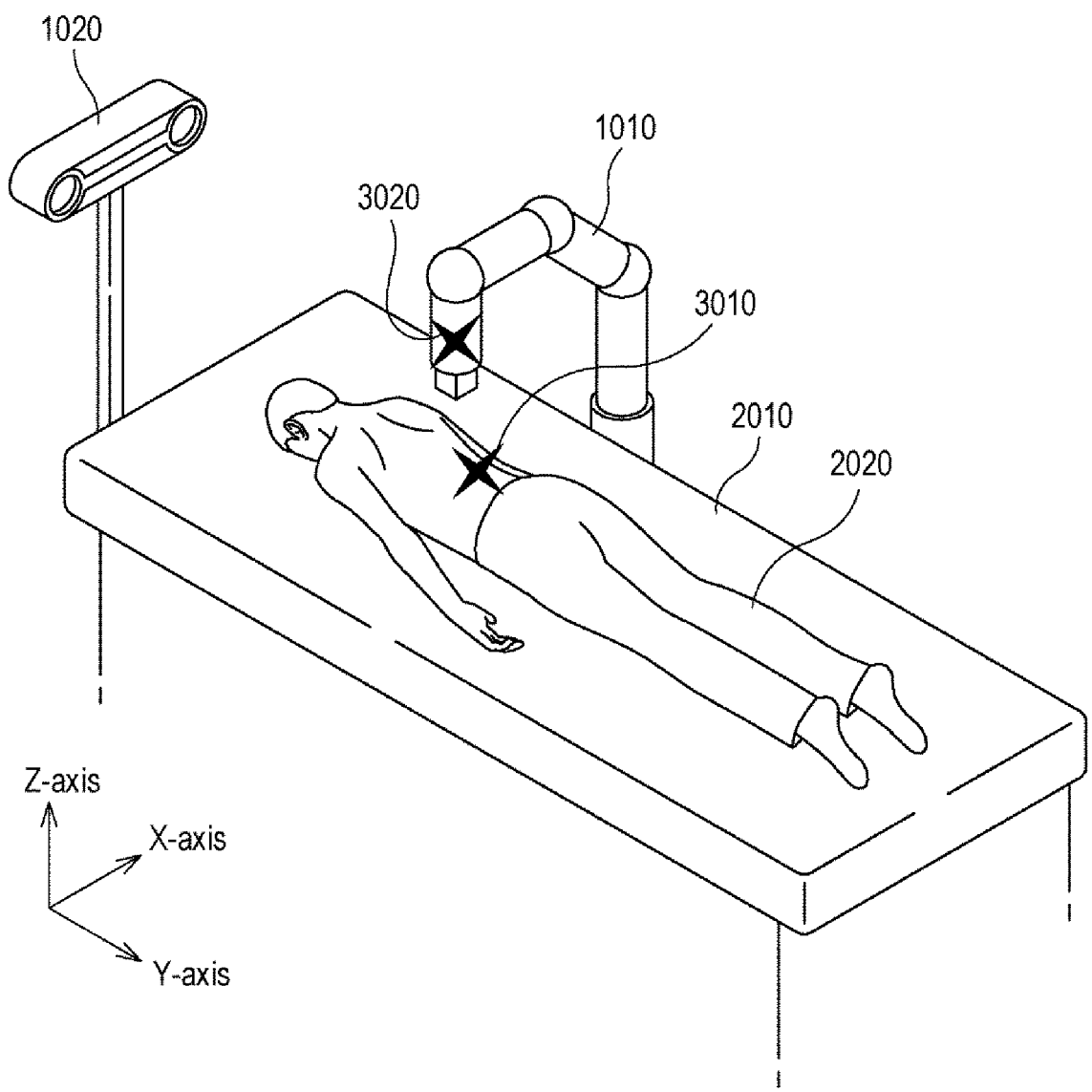
FIG. 2 is a diagram showing an example in which the image matching device according to an embodiment of the present disclosure is used for surgery.

FIG. 2 is a diagram showing an example in which the image matching device according to an embodiment of the present disclosure is used for surgery.

As described above, the image matching device may generate the virtual vertebrae measurement image for the patient by using the dorsal surface scan image obtained from the patient and the human body correlation model.

FIG. 2 shows a state in which the image matching device according to any one of the above-described embodiments is used for a patient 2020 supported on a surgery table 2010. As shown in FIG. 2, the image matching device according to one embodiment may include a 3D scanner 1010, a tracking sensor 1020, a memory and/or a processor.

Specifically, the patient 2020 subject to surgery may be supported on a surgery table 2010. A reference marker 3010 may be fixed to the body of the patient supported on the surgery table 2010. As described above, the reference marker 3010 may be fixedly installed on one of the vertebral bones of the patient. A scanner marker 3020 may be attached to the 3D scanner 1010. The scanner marker 3020 may be used to obtain information on a scanning point of the 3D scanner 1010.

The 3D scanner 1010 may three-dimensionally scan the dorsal surface of the patient supported on the surgery table. In this case, the dorsal surface of the patient supported on the surgery table may be scanned in an intra-operative posture. Accordingly, the 3D scanner 1010 may obtain a dorsal surface scan image of the patient in the intra-operative posture. The posture of the patient in the intra-operative posture may be referred to as a first posture in some embodiments.

The 3D scanner 1010 may be installed, for example, in a direction in which the 3D scanner 1010 faces the top plate of the surgery table 2010 from above on the z axis of the surgery table 2010. Accordingly, the 3D scanner 1010 may face the top plate of the surgery table 2010 so as to scan the body of the patient 2020 supported on the surgery table 2010. The position of the 3D scanner 1010 may be changed in some embodiments.

The tracking sensor 1020 may obtain the position and posture information of the reference marker 3010 and the position and posture information of the scanner marker 3020. The tracking sensor 1020 may be installed, for example, in a direction in which the tracking sensor 1020 faces the surgery table 2010 from above or below on the y axis of the surgery table. That is, the tracking sensor 1020 may be installed in the direction of the head or foot of the patient supported on the surgery table so as to track the position and posture of the reference marker 3010 fixed to the body of the patient and/or the position and posture of the scanner marker 3020 attached to the 3D scanner 1010. The position of the tracking sensor 1020 may vary depending on the embodiments.

The memory may store the human body correlation models according to the above-described embodiments. In some embodiments, the memory may store at least one of the human body correlation models according to the above-described embodiments. The memory is not shown in this utilization example.

The processor may obtain a dorsal surface scan image of a target patient from the 3D scanner 1010. The processor may also obtain a human body correlation model from the memory. The processor may generate a virtual vertebrae measurement image by applying the obtained dorsal surface scan image to the human body correlation model. The processor is not shown in this utilization example.

Specifically, the processor may extract information on the shape of the dorsal surface of the target patient from the received dorsal surface scan image. The information on the dorsal surface shape extracted in this operation may be information indicating the dorsal surface shape of the target patient. Specifically, the information on the dorsal surface shape may be information indicating the shape of the dorsal surface when the target patient takes an intra-operative posture while being supported on the surgery table.

In addition, the processor may input the extracted dorsal surface shape information of the target patient into the received human body correlation model and may obtain an estimated vertebrae position value when the dorsal surface takes the corresponding shape. Information on the estimated vertebrae position when the target patient takes an intra-operative posture may be obtained through this process.

The processor may generate a virtual vertebrae measurement image by using the information on the estimated vertebrae position. The generated virtual spine measurement image may be obtained by estimating the vertebrae position when the target patient takes an intra-operative posture and converting the vertebrae position into an image as if it is an actually captured vertebrae measurement image.

The processor may match the generated virtual vertebrae measurement image with the body of the patient. That is, in the matching process, the processor may use the position and posture information of the reference marker 3010 and the position and posture information of the scanner marker 3020 obtained by the tracking sensor 1020. In the matching process, the coordinate system of the virtual vertebrae measurement image may be matched with the coordinate system of the body of the patient. Accordingly, based on the estimated vertebrae position shown in the matched virtual vertebrae measurement image, the body of the actual patient may be subjected to surgery.

Figure 3:
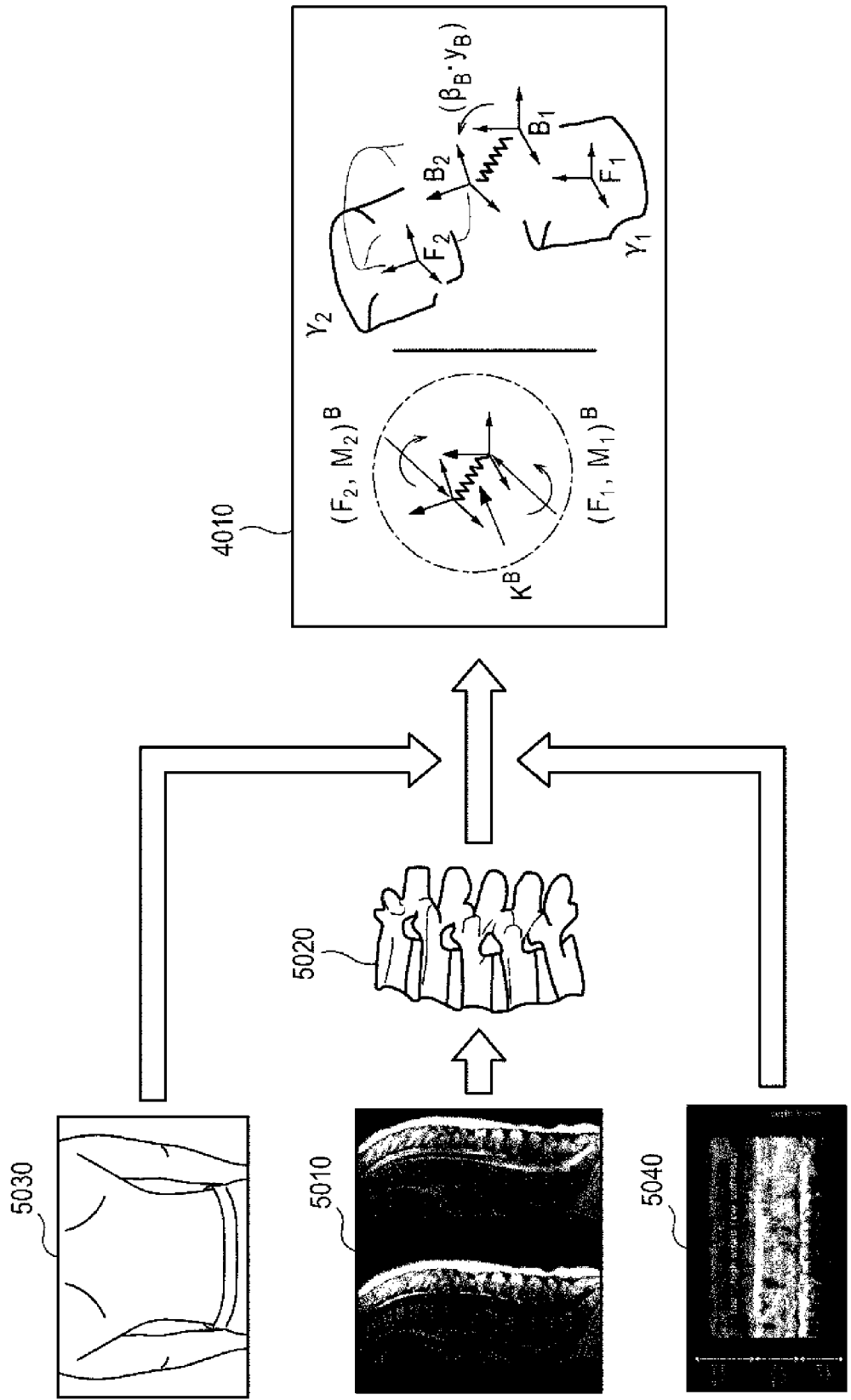
FIG. 3 is a diagram showing a process of generating a human body correlation model according to an embodiment of the present disclosure.

FIG. 3 is a diagram showing the process of generating the human body correlation model according to an embodiment of the present disclosure.

As described above, the human body correlation model may be a model on the correlation between the dorsal surface and the vertebrae of the human body. Specifically, the human body correlation model may indicate a relationship between the shape of the dorsal surface and the vertebrae position inside the body of the patient in the shape of the dorsal surface.

As used herein, the term "vertebrae position" may mean a position of the vertebrae in the body of the patient, or may mean, according to the context, an arrangement position or shape of the vertebrae when the vertebral soft tissues are contracted or relaxed.

As shown in FIG. 3, the human body correlation model may be generated by using the dorsal surface scan image obtained by scanning the dorsal surface and the vertebrae measurement image 5010 obtained by capturing an image of the vertebrae at the same moment. Specifically, the human body correlation model may be generated by obtaining a correlation between the dorsal surface and the vertebrae based on the dorsal surface shape information 5030 obtained from the dorsal surface scan image and the vertebrae position information obtained from the vertebrae measurement image 5010. In some embodiments, the vertebral soft tissue properties 5040 of the patient may be further used in the process of generating the human body correlation model.

The vertebrae measurement image 5010, the dorsal surface shape information 5030 and/or the vertebral soft tissue properties 5040 may be data about a body of one patient. For example, in the case of generating the above-described patient-specific human body correlation model, the vertebrae measurement image used for generation of the patient-specific human body correlation model may be a vertebrae measurement image of a patient to be subjected to surgery, the dorsal surface shape information may be information obtained from the dorsal surface of the patient, and the vertebral soft tissue properties may be properties measured for the vertebral soft tissues of the patient.

First, a vertebrae 3D model 5020 of the vertebrae of the human body may be generated by using the vertebrae measurement image 5010. As used herein, the term "vertebrae measurement image 5010" may mean a CTA image, a CT image and/or an MRI image obtained by capturing an image of the vertebrae of the human body. The generated vertebrae 3D model 5020 may be obtained by three-dimensionally modeling the shape of the vertebrae, i.e., the hard tissues such as vertebral bones or the like and/or the soft tissues between the vertebral bones.

Thereafter, a dorsal surface shape value corresponding to the vertebrae position may be measured. The shape of the dorsal surface of the human body may vary depending on the arrangement positions of the vertebral bones and the vertebral soft tissues. By measuring the dorsal surface shape corresponding to the vertebrae position, information on the correlation between the vertebrae position and the dorsal surface shape may be obtained. The correlation information may be a constitutive equation which indicates a physical relationship between the information on the vertebrae position obtained from the vertebrae measurement image 5010 and the dorsal surface shape information 5030 obtained from the dorsal surface scan image.

The obtained correlation information may be reflected in the above-described vertebrae 3D model 5020. The human body correlation model 4010 may be generated as the correlation information between the vertebrae position and the dorsal surface shape is reflected in the above-described vertebrae 3D model 5020.

In this process, the human body correlation model 4010 generated through the correlation information and the vertebrae 3D model 5020 may be a dynamic model for the vertebrae. That is, the human body correlation model may predict the change in the vertebrae position depending on the change in the dorsal surface shape. For example, when time-series information on the dorsal surface shape is inputted to the human body correlation model, the human body correlation model may output a change in the vertebrae position that varies over time. Accordingly, the human body correlation model may predict the changed vertebrae position even if a motion or a posture change occurs during the surgery of the patient.

In one embodiment, the measurement of the dorsal surface shape value corresponding to the vertebrae position may be repeatedly performed a plurality of times. That is, the dorsal surface shape corresponding to each vertebrae position may be measured while changing the vertebrae position by changing the posture of the patient. Accordingly, multiple pieces of correlation information may be obtained and reflected in the human body correlation model 4010. As correlation information is obtained at various vertebrae positions, the human body correlation model 4010 generated thereafter may more accurately estimate the dorsal surface shape corresponding to the vertebrae position.

In an embodiment, a plurality of dorsal surface scan images may be obtained in chronological order from the dorsal surface shape when the vertebrae moves in a specific direction, and multiple pieces of correlation information obtained from the dorsal surface shape may be reflected in the human body correlation model. In this way, when the vertebrae moves in a specific direction, the chronological change process of the dorsal surface shape may be reflected in the human body correlation model.

In one embodiment, the correlation information may be obtained by obtaining a solution of a partial differential equation according to the Finite Element Method (FEM). Specifically, the relationship between the vertebrae position and the dorsal surface shape may be represented by a partial differential equation of the dorsal surface shape value using the vertebrae position as a variable, or a partial differential equation of the vertebrae position using the dorsal surface shape value as a variable. By obtaining an approximate solution of the partial differential equation according to the finite element method, the correlation information between the vertebrae position and the dorsal surface shape may be obtained.

In one embodiment, a human body correlation model 4010 may be generated by further reflecting the soft tissue properties 5040 measured from the patient vertebrae. Specifically, the vertebral soft tissue properties 5040 of the patient may be taken into account in the process of generating the human body correlation model 4010 based on the correlation of the dorsal surface shape according to the above-described vertebrae position. As used herein, the term "vertebral soft tissue" may refer to soft tissues adjacent to vertebral bones, such as muscles, tendons and ligaments surrounding the vertebral bones. The soft tissue properties may generally refer to physical properties such as elasticity, shrinkage coefficient and the like of the soft tissues, and/or chemical and biological properties of substances constituting the soft tissues. The soft tissue properties may vary from patient to patient.

First, hard tissues such as vertebral bones and the like may be distinguished from soft tissues described above. When the vertebrae of the patient contracts or relaxes in a specific direction, even if the movement is made in the same direction, the arrangement positions of the vertebral hard tissues may vary depending on the vertebral soft tissue properties of the patient. In addition, even in the same vertebral hard tissue arrangement, the dorsal surface shape at that time may vary depending on the vertebral soft tissue properties of the patient.

Therefore, when the human body correlation model is generated by reflecting the vertebrae measurement image and/or the dorsal surface scan image, if the vertebral soft tissue properties of the patient are reflected, it is possible to generate a human body correlation model as a dynamic model capable of more accurately estimating the dorsal surface shape corresponding to the vertebrae position. For example, a human body correlation model may be generated by obtaining a more specific correlation on the direction and degree of contraction of the soft tissues corresponding to the vertebrae position and the resultant dorsal surface shape.

In this regard, the vertebral soft tissue properties 5040 may be measured by imaging the elasticity-related characteristics and stiffness of the soft tissues. For this purpose, a USE (Ultrasound Elastography) method may be used.

In one embodiment, a deep learning method may be used to derive correlation information on the dorsal surface shape corresponding to the vertebrae position. As used herein, the term "deep learning" is a field of machine learning and is a method in which when raw data is directly inputted to a computer, a deep learning algorithm understands the data based on artificial neural networks and extracts a high level of abstracted information. Based on the deep learning method, vertebrae position information in the form of big data and information on the dorsal surface shape may be used to extract information on a correlation between the two pieces of information. If the correlation information obtained through the deep learning is used at the time of generating the human body correlation model, it is possible to increase the accuracy of the correlation of the vertebrae position and the dorsal surface shape.

In one embodiment, the human body correlation model may be generated by capturing patient vertebrae images at different frequencies without having to use the 3D scan image of the dorsal surface of the patient. In an image capturing technique such as CT or the like, the human body may be imaged so that hard tissues such as bones, teeth and the like or soft tissues such as skin and the like may be well expressed according to the frequency at the time of image capturing. In this operation, the vertebrae image captured so that the soft tissues are well expressed may replace the dorsal surface scan image described above. A correlation between the dorsal surface and the vertebrae may be obtained by using the vertebrae image captured so that the hard tissues are well expressed and the vertebrae image captured so that the soft tissues are well expressed. A human body correlation model may be generated based on the correlation between the dorsal surface and the vertebrae.

Figure 4:
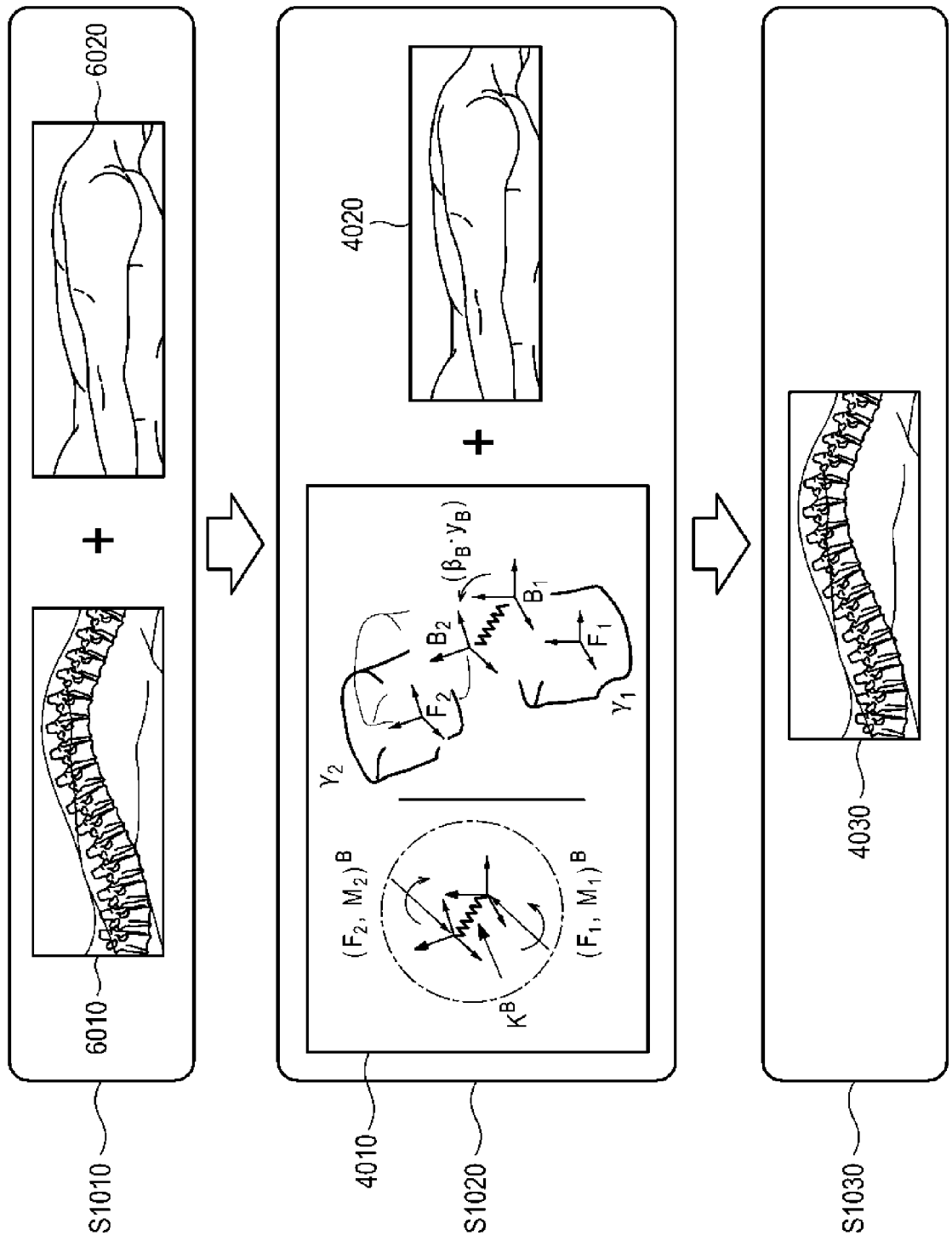
FIG. 4 is a diagram showing a process of generating and utilizing a patient-specific human body correlation model according to an embodiment of the present disclosure.

FIG. 4 is a diagram showing a process of generating and utilizing a patient-specific human body correlation model according to an embodiment of the present disclosure.

As described above, the human body correlation model may be a patient-specific human body correlation model. The patient-specific human body correlation model may be a human body correlation model in accordance with the correlation between the dorsal surface and the vertebrae of a patient to be subjected to surgery.

The patient-specific human body correlation model may be generated based on the vertebrae measurement image 6010 and/or the dorsal surface scan image 6020 previously obtained from the patient before surgery. In this regard, the vertebrae measurement image 6010 of the patient obtained before surgery may be referred to as a second vertebrae measurement image, and the dorsal surface scan image 6020 of the patient obtained before surgery may be referred to as a second dorsal surface scan image.

Specifically, the process of generating and utilizing the patient-specific human body correlation model shown in FIG. 4 may include a step (S1010) of obtaining correlation information between a pre-surgical vertebrae measurement image 6010 and a pre-surgical dorsal surface scan image 6020 of a patient to be subjected to surgery, a step (S1020) of applying an intra-operative dorsal surface scan image 4020 of the patient to a patient-specific human body correlation model 4010 generated based on the correlation information, and/or a step (S1030) of generating a virtual vertebrae measurement image (4030).

First, the pre-surgical vertebrae measurement image 6010 and the pre-surgical dorsal surface scan image 6020 of the patient to be subjected to surgery may be obtained. In this regard, the pre-surgical vertebrae measurement image 6010 may be a vertebrae measurement image previously obtained from the patient before surgery. In addition, the pre-surgical dorsal surface scan image 6020 may be a dorsal surface scan image of the patient obtained in the posture of the patient when the pre-surgical vertebrae measurement image 6010 is obtained.

Correlation information between the vertebrae position information obtained from the pre-surgical vertebrae measurement image 6010 and the dorsal surface shape information obtained from the pre-surgical dorsal surface scan image 6020 is obtained. Based on the correlation information, a patient-specific human body correlation model 4010 may be generated. The process of generating the patient-specific human body correlation model 4010 conforms to the above-described process of generating the human body correlation model. The vertebrae image used in this process may be the pre-surgical vertebrae measurement image 6010, and the dorsal surface information may be information obtained from the pre-surgical dorsal surface scan image 6020.

The dorsal surface scan image 4020 obtained during surgery may be applied to the generated patient-specific human body correlation model 4010. The dorsal surface scan image 4020 obtained during surgery may be a dorsal surface scan image obtained from an intra-operative posture of a target patient supported on a surgery table. The dorsal surface scan image 4020 may be obtained from the dorsal surface of the target patient at least once immediately before or during surgery of the target patient.

The pre-surgical vertebrae measurement image 6010 and the pre-surgical dorsal surface scan image 6020, which are previously obtained and used as the basis for generation of the patient-specific human body correlation model, may be obtained in a posture different from the intra-operative posture of the target. That is, the posture taken by the patient while being supported on the surgery table during surgery may be different from the posture of the patient when the pre-surgical vertebrae measurement image 6010 and the pre-surgical dorsal surface scan image 6020 are obtained from the patient. In this regard, the posture of the patient supported on the surgery table during surgery may be referred to as a first posture as described above. The posture of the patient when the pre-surgical vertebrae measurement image 6010 and the pre-surgical dorsal surface scan image 6020 are obtained may be referred to as a second posture.

A virtual vertebrae measurement image 4030 may be generated by applying the intra-operative dorsal surface scan image 4020 to the patient-specific human body correlation model 4010 of the target patient. The virtual vertebrae measurement image 4030 may estimate and display the vertebrae position in the intra-operative posture of the target patient supported on the surgery table.

In one embodiment, as described above, the processor of the image matching device may not use the patient-specific human body correlation model stored in the memory, but may directly generate a patient-specific human body correlation model based on the pre-surgical vertebrae measurement image 6010 and the pre-surgical dorsal surface scan image 6020. In this case, the memory of the image matching device may store the pre-surgical vertebrae measurement image 6010 and the pre-surgical dorsal surface scan image 6020. The processor may receive the pre-surgical vertebrae measurement image 6010 and the pre-surgical dorsal surface scan image 6020 from the memory and may directly generate a patient-specific human body correlation model.

In one embodiment, the pre-surgical vertebrae measurement image 6010 and the pre-surgical dorsal surface scan image 6020 of the target patient may have been previously obtained using an optical marker. The optical marker may be attached around the affected part of the dorsal surface of the target patient when capturing the pre-surgical vertebrae measurement image 6010. In some embodiments, the optical marker may have a rectangular ring shape with an empty center. Markers for emitting light may be attached side by side to the respective sides of the rectangle side. When capturing the pre-surgical vertebrae measurement image 6010, simultaneously with the acquisition of the vertebrae measurement image, the shape of the dorsal surface may be obtained from the optical marker attached to the target patient. Thereafter, the optical marker may be attached to the surgical site of the patient during the actual surgery in the same manner, and the surgery may be performed while obtaining the dorsal surface shape of the patient in real time. The dorsal surface shape of the patient obtained from the optical marker may be used to generate a virtual vertebrae measurement image for estimating the vertebrae position in real time.

In one embodiment, when generating a patient-specific human body correlation model, the vertebral soft tissue properties measured from the patient to be subjected to surgery may be further utilized. By reflecting the vertebral soft tissue properties of the patient in the human body correlation model, it is possible to generate the patient-specific human body correlation model in such a form as to further reflect the human body characteristics of the patient under surgery.

Figure 5:
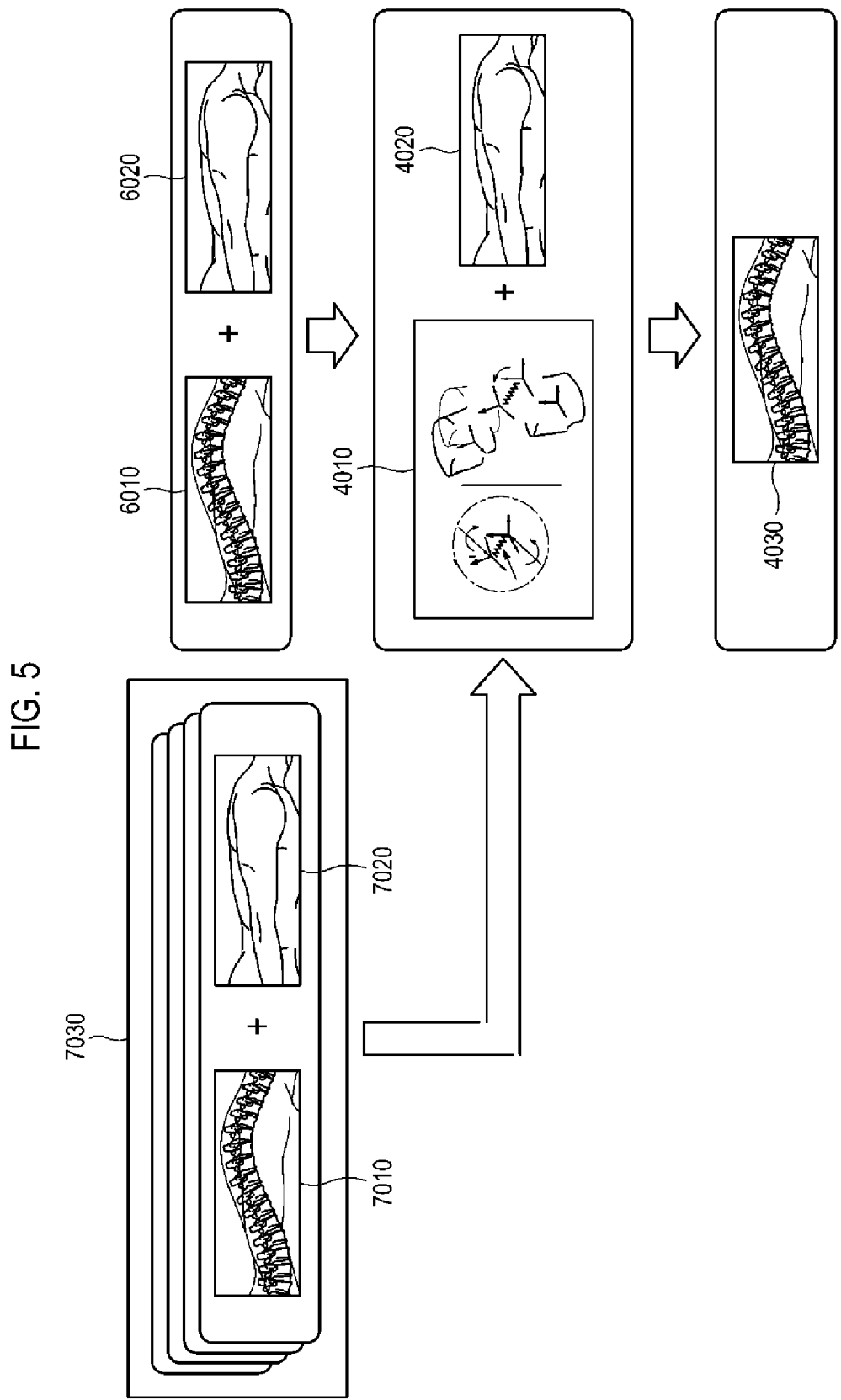
FIG. 5 is a diagram showing a process of generating and utilizing a database-based human body correlation model according to an embodiment of the present disclosure.

FIG. 5 is a diagram showing a process of generating and utilizing a database-based human body correlation model according to an embodiment of the present disclosure.

As described above, the human body correlation model may be a database-based human body correlation model. The database-based human body correlation model may be a human body correlation model that represents an average correlation between the vertebrae position and the dorsal surface of the human body based on at least one data of the vertebrae and the dorsal surface accumulated in the database 7030.

The database-based human body correlation model may be generated by correcting the aforementioned patient-specific human body correlation model using the dorsal surface scan image 7020 and/or the vertebrae measurement image 7010 stored in the database 7030. In this regard, the vertebrae measurement image 7010 of the patient selected from the database may be referred to as a third vertebrae measurement image, and the dorsal surface scan image 7020 of the patient selected from the database may be called a third dorsal surface scan image.

Specifically, the process of generating and utilizing the patient-specific human body correlation model shown in FIG. 5 may include a process of generating a patient-specific human body correlation model, correcting the patient-specific human body correlation model using the data of the database 7030 to generate a database-based human body correlation model 4010, and generating a virtual vertebrae measurement image 4030 using the database-based human body correlation model 4010.

First, a patient-specific human body correlation model may be generated based on the pre-surgical vertebrae measurement image 6010 and the pre-surgical dorsal surface scan image 6020 of the target patient. The generation of the patient-specific human body correlation model may be performed as described above.

Subsequently, the patient-specific human body correlation model described above may be corrected using the vertebrae measurement image 7010 and/or the dorsal surface scan image 7020 for at least one patient selected among a group of different patients stored in the database 7030. The database 7030 may store vertebrae images and/or dorsal surface scan images corresponding to the vertebrae images, which are obtained from the human bodies of a plurality of other patients. In this regard, the dorsal surface scan images corresponding to the vertebrae images may refer to images obtained by scanning the dorsal surfaces of the patients with the 3D scanner at the time of obtaining the vertebrae images.

Specifically, vertebrae position information may be obtained from the vertebrae measurement image 7010 obtained from the database 7030, and dorsal surface shape information may be obtained from the corresponding dorsal surface scan image 7020. Correlation information may be derived from the vertebrae position information and the dorsal surface shape information. The correlation information may be reflected in the previously generated patient-specific human body correlation model.

The patient selected from the database 7030 for generation of the database-based human body correlation model may be a patient who is not the patient to be subjected to surgery. In addition, the number of patients selected from the database 7030 may be plural. As the number of selected patients grows larger, the generated human body correlation model can more accurately estimate the dorsal surface shape corresponding to the vertebrae position.

A virtual vertebrae measurement image 4030 may be generated by applying the dorsal surface scan image 4020 obtained during the surgery of the target patient to the database-based human body correlation model 4010 generated through this process.

In one embodiment, as described above, the processor of the image matching device may not use the previously generated database-based human body correlation model stored in the memory, but may generate a database-based human body correlation model 4010 by directly correcting the patient-specific human body correlation model stored in the memory. In this case, the memory of the image matching device may store patient-specific human body correlation models.

In one embodiment, when the processor of the image matching device directly generates a database-based human body correlation model, the memory may serve as the database 7030 described above. In this case, the memory may store the vertebrae measurement images 7010 and/or the dorsal surface scan images 7020 of a plurality of other patients.

In one embodiment, when the processor of the image matching device directly generates the database-based human body correlation model, the above-described network interface may receive data necessary for generating the database-based human body correlation model from a server. That is, the network interface may communicate with the server acting as the database 7030, may receive the vertebrae measurement image 7010 and/or the dorsal surface scan image 7020, and may transmit them to the processor. The processor may generate a database-based human body correlation model using the received data.

In one embodiment, the database-based human body correlation model may be generated using big data technique. As used herein, the term "big data technique" may refer to a technique for extracting features or patterns from a large set of structured or unstructured data and analyzing the result. Information about the vertebrae and the dorsal surface of other patients may be obtained using the big data technique. The patient-specific human body correlation model may be corrected by using the vertebrae information and the dorsal surface information in the form of big data to generate a database-based human body correlation model.

In one embodiment, the database-based human body correlation model may be generated by excluding information on the vertebrae and the dorsal surface of the patient to be subjected to surgery. As described above, the database-based human body correlation model may be generated by correcting the patient-specific human body correlation model. In some embodiments, the database-based human body correlation model may be generated by using only the information about a plurality of patients obtained from the database without having to use the patient-specific human body correlation model. In this case, the database-based human body correlation model may be generated by using the vertebrae position information and the dorsal surface information of a plurality of patients according to the above-described process of generating the human body correlation model.

In one embodiment, the patient selected from the database may be a patient of a patient group to which the patient to be subjected to surgery belongs. As used herein, the term "patient group" may mean a group of a plurality of patients classified based on the characteristics of the patients. For example, if the patient to be subjected to surgery is a 45 year old man, the patient selected from the database to generate the database-based human body correlation model may be a male patient in his forties.

In one embodiment, even when generating the database-based human body correlation model, the previously measured vertebral soft tissue properties of the patient selected from the database may be utilized. If the vertebral soft tissue properties of the selected patient as well as the information on the vertebrae and the dorsal surface of the selected patient are present in the database 7030, the soft tissue properties may also be used to correct the patient-specific human body correlation model.

Figure 6:
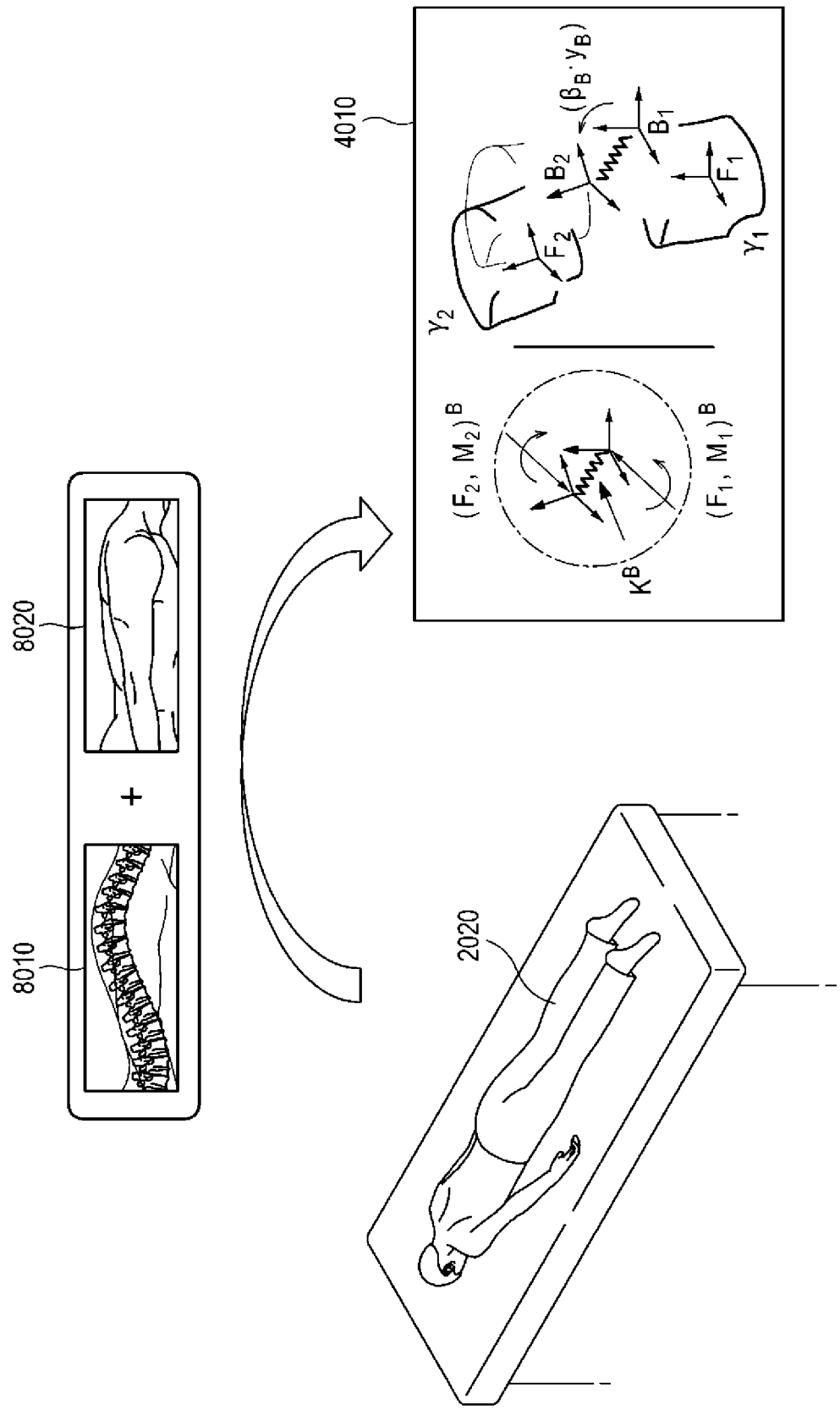
FIG. 6 is a diagram showing a process of correcting the human body correlation model according to an embodiment of the present disclosure.

FIG. 6 is a diagram showing a process of correcting the human body correlation model according to an embodiment of the present disclosure.

As described above, the human body correlation model may be further corrected based on the posture of the patient to be subjected to surgery. That is, the processor of the image matching device may further correct the above-described human body correlation model based on additional information obtained from the intra-operative posture of the patient supported on the surgery table. In this regard, the human body correlation model to be corrected may be a human body correlation model according to any embodiment of the present disclosure, such as the patient-specific human body correlation model, the database-based human body correlation model or the like.

The process of correction may be performed in such a way that a vertebrae measurement image 8010 and a dorsal surface scan image 8020 are obtained from an intra-operative posture (first posture) of a patient 2020 supported on a surgery table, and the human body correlation model is corrected based on the vertebrae measurement image 8010 and the dorsal surface scan image 8020. In this regard, the vertebrae measurement image 8010 captured in the intra-operative posture (first posture) of the patient 2020 supported on the surgery table may be referred to as a fourth vertebrae measurement image. The dorsal surface scan image 8020 of the patient captured in the intra-operative posture may be the same as the intra-operative dorsal surface scan image 4020 described above and may be referred to as a first dorsal surface scan image.

The correction of the human body correlation model may be performed to reflect the information on the vertebrae position and the dorsal surface in the intra-operative posture of the patient in the human body correlation model. The vertebrae measurement image 6010 and the dorsal surface scan image 6020 used for the generation of the patient-specific human body correlation model of the target patient described above may be obtained before surgery in an environment different from the intra-operative environment. In addition, the posture (e.g., the second posture) of the patient at the time of obtaining such information may differ from the intra-operative posture (the first posture) taken by the patient 2020 supported on the surgery table. Accordingly, by obtaining a vertebrae measurement image 8010 and a dorsal surface scan image 8020 for a patient in an intra-operative posture before the start of surgery and feeding back the correlation between the two images to the human body correlation model, it is possible to further increase the accuracy of the human body correlation model.

Specifically, the vertebrae measurement image 8010 may be obtained from the patient 2020 supported on the surgery table in an intra-operative posture (first posture). In order to obtain the spine measurement image, the image matching device may further include a vertebrae image camera. The vertebrae image camera may be installed to capture the vertebrae measurement image 8010 of the patient supported on the surgery table. The vertebrae image camera may obtain the vertebrae measurement image 8010 of the patient in the intra-operative posture.

In addition, as described above, the 3D scanner may three-dimensionally scan the dorsal surface of the patient supported on the surgery table in the intra-operative posture (first posture). The dorsal surface scan image 8020 of the patient taking the intra-operative posture may be obtained through this process. The dorsal surface scan image 8020 may be the same as the dorsal surface scan image 4020 captured in the intra-operative posture.

The processor may obtain vertebrae position information and dorsal surface shape information in the intra-operative posture from the vertebrae measurement image 8010 and the dorsal surface scan image 8020 captured in the intra-operative posture. The processor may use the vertebrae position information and the dorsal surface shape information to obtain correlation information between them. Thereafter, the processor may correct the human body correlation model using the obtained correlation information.

The correction of the human body correlation model using the correlation information may be performed by comparing the dorsal surface shape information obtained by inputting the vertebrae position information in the intra-operative posture into the human body correlation model and the dorsal surface shape information obtained from the actual dorsal surface scan image. If a difference between the outputted dorsal surface shape information and the actual dorsal surface shape information is equal to or larger than a predetermined threshold value, correction may be performed. The correction may be performed by deriving a correlation between the actual vertebrae position information and the actual dorsal surface shape, giving weight to the correlation, and additionally reflecting the weighted correlation in an existing human body correlation model.

Thereafter, the processor may generate the above-described virtual vertebrae measurement image by using the human body correlation model 4010 corrected for the intra-operative posture.

In one embodiment, the processor may repeatedly perform the correction of the human body correlation model a predetermined number of times based on the information obtained in the intra-operative posture. In this case, in order to perform the correction a plurality of times, the 3D scanner may three-dimensionally scan the dorsal surface of the patient in the intra-operative posture a plurality of times, and the vertebrae image camera may repeatedly capture an image of the vertebrae of the patient in the intra-operative posture a plurality of times.

Figure 7:
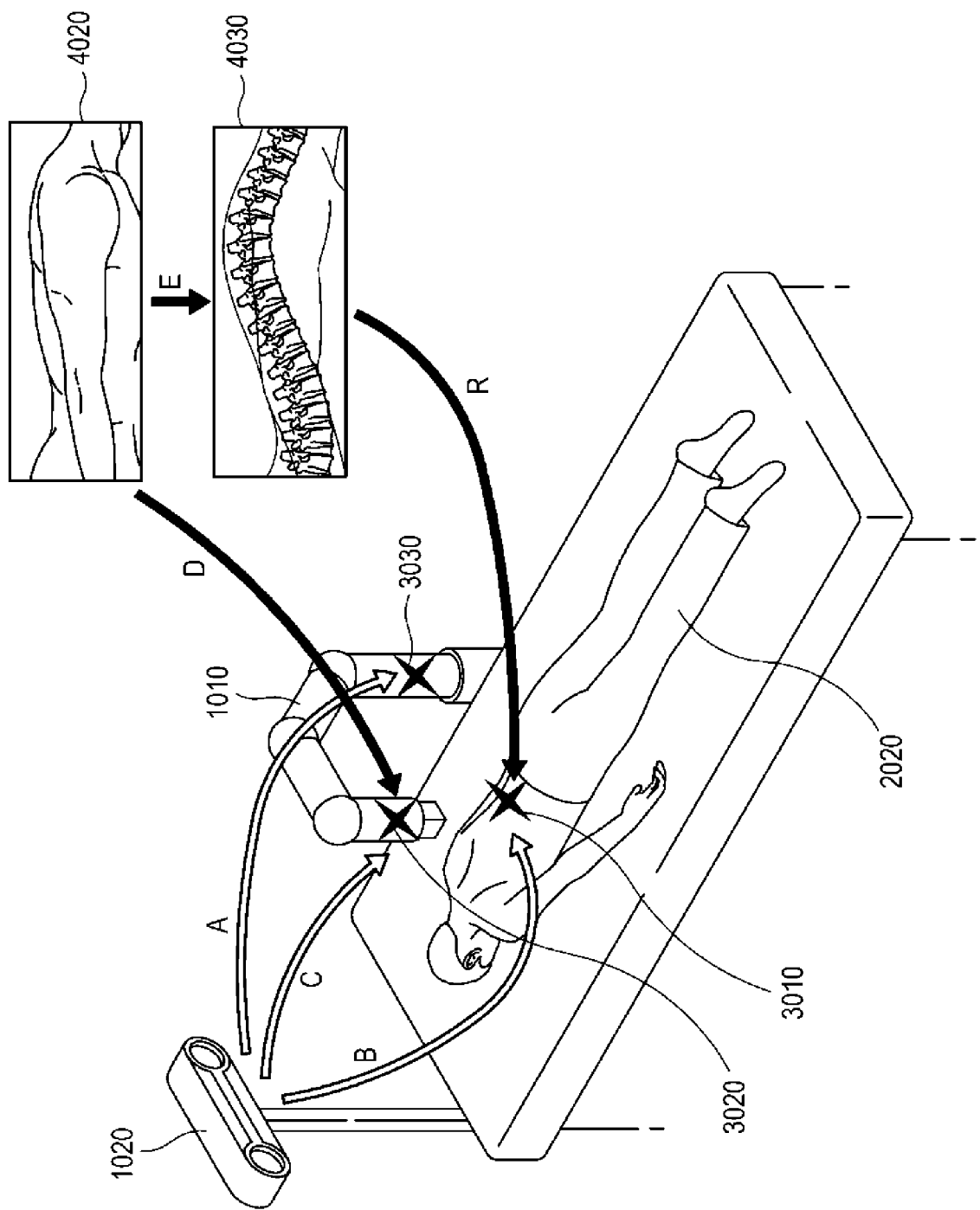
FIG. 7 is a diagram showing a process of matching a virtual vertebrae measurement image with a body of a patient according to an embodiment of the present disclosure.

FIG. 7 is a diagram showing a process of matching the virtual vertebrae measurement image with the body of the patient according to an embodiment of the present disclosure.

As described above, the processor may match the generated virtual vertebrae measurement image 4030 with the body of the patient 2020. As the virtual vertebrae measurement image 4030 is matched with the patient 2020, the processor may know the actual position of the body of the patient 2020 corresponding to the vertebrae position estimated by the virtual vertebrae measurement image 4030. Thus, the processor may transmit a control signal to the robot arm or the like.

As used herein, the term "matching" may mean an act of matching the coordinate system of the virtual vertebrae measurement image 4030 with the coordinate system of the body of the patient 2020. The position and posture information of the reference marker 3010 obtained by the tracking sensor 1020, the position and posture information of the scanner marker 3020, the dorsal surface scan image 4020, and/or the virtual vertebrae measurement image 4030 may be used for matching purposes.

Specifically, the tracking sensor 1020 may obtain the position and posture information B of the reference marker 3010 and/or the position and posture information C of the scanner marker 3020. The processor may receive the position and posture information B of the reference marker and/or the position and posture information C of the scanner marker from the tracking sensor 1020.

As described above, the reference marker 3010 is a marker fixedly installed on the body of the patient and may be a marker that serves as a reference point of the coordinate system of the patient. Furthermore, the scanner marker 3020 is a marker attached to the 3D scanner 1010 and may be used to indicate a point scanned by the 3D scanner. In some embodiments, the scanner marker 3020 may be attached to the end of the 3D scanner 1010.

The processor may define the patient coordinate system based on the reference marker 3010 fixed to the body of the patient. The positions of surgical devices such as a robot arm and the like may be indicated on the defined patient coordinate system. In some embodiments, this process may be described as the coordinate system of the surgical device (e.g., the robot arm) matched with the patient coordinate system.

The position information of a specific marker obtained by the tracking sensor 1020 may mean a position coordinate of the specific marker on the patient coordinate system defined based on the reference marker 3010. In some embodiments, the coordinate system may mean an orthogonal position coordinate system represented by x, y and z axes. The position coordinates may mean spatial coordinates indicating x, y and z positions on a coordinate system.

The posture information of a specific marker obtained by the tracking sensor 1020 may refer to a posture of the specific marker located on the patient coordinate system, which is defined as roll, pitch and yaw. Roll, pitch and yaw have been described above.

In some embodiments, an additional marker 3030 may be further attached to the 3D scanner 1010. The tracking sensor 1020 may obtain the position and posture information A of the additional marker and may transmit the information to the processor. Using the position and posture information of the additional marker, accurate information about the current scanning point of the 3D scanner 1010 may be transmitted to the processor.

In the matching process, the processor may further obtain information about a coordinate transformation relationship D between the dorsal surface scan image 4020 and the scanning point of the 3D scanner 1010 and/or a coordinate transformation relationship E between the dorsal surface scan image 4020 and the virtual vertebrae measurement image 4030.

The dorsal surface scan image 4020 used herein is a dorsal surface scan image obtained for the intra-operative posture (first posture) of the patient 2020 supported on the surgery table and may correspond to the above-described first dorsal surface scan image.

The coordinate transformation relationship D may mean a coordinate transformation relationship between the dorsal surface scan image 4020 and the scanning point of the 3D scanner 1010 that scans the dorsal surface scan image. In this regard, the scanning point of the 3D scanner 1010 may be represented by the position and posture of the scanner marker 3020 attached to the 3D scanner. Through the coordinate transformation relationship D, it is possible to know a mathematical relationship about which part of the dorsal surface of the patient is scanned in a real space to obtain one point on the dorsal surface scan image 4020. This coordinate transformation relationship D may be referred to as a first coordinate transformation relationship. The processor may obtain the coordinate transformation relationship D from the 3D scanner 1010.

The coordinate transformation relationship E may mean a coordinate transformation relationship between the dorsal surface scan image 4020 and the virtual vertebrae measurement image 4030 generated based on the dorsal surface scan image. Through the coordinate transformation relationship E, it is possible to know a mathematical relationship about which part of the virtual vertebrae measurement image 4030 corresponds to one point of the dorsal surface scan image 4020. This coordinate transformation relationship E may be referred to as a second coordinate transformation relationship. The processor may obtain the coordinate transformation relationship E in the process of generating the virtual vertebrae measurement image 4030 from the dorsal surface scan image 4020.

The processor may obtain a coordinate transformation relationship R from the virtual vertebrae measurement image 4030 to the position and posture information of the reference marker 3010 using the obtained position and posture information B of the reference marker, the position and posture information C of the scanner marker, the coordinate transformation relationship D and/or the coordinate transformation relationship E. The coordinate transformation relationship R may be a mathematical relation about which point of the virtual vertebrae measurement image 4030 is converted to a point on the patient coordinate system in the real space. By obtaining the coordinate transformation relationship R for the position and posture information of the reference marker, which serves as a reference of the patient coordinate system, it is possible to know which part of the body of the patent 2020 should be matched with the virtual vertebrae measurement image 4030.

In some embodiments, the position and posture information of the markers may also be expressed in coordinate transformation relationships. As described above, the tracking sensor 1020 may sense the position and the posture of the reference marker 3010 to obtain the position and posture information B of the reference marker. In this case, the position and posture information B of the reference marker may be regarded as a coordinate transformation relationship B from the tracking sensor 1020 to the position and posture information of the reference marker. Similarly, the position and posture information C of the scanner marker may be regarded as a coordinate transformation relationship C from the tracking sensor 1020 to the position and posture information of the scanner marker.

In some embodiments, the coordinate transformation relationships may be represented as coordinate transformation matrices. In addition, depending on the definition method, the coordinate transformation relationships may be defined as the inverse transformation relationships of the coordinate transformation relationships. For example, the coordinate transformation relationship E is a coordinate transformation relationship from the dorsal surface scan image 4020 to the virtual vertebrae measurement image 4030. However, depending on the definition method, the coordinate transformation relationship E may be defined as a coordinate transformation relationship from the virtual vertebrae measurement image 4030 to the dorsal surface scan image 4020.

As described above, the equation for obtaining the coordinate transformation relationship R may be as follows. In this regard, T (Transformation) may be an intermediate variable for making an equation.

$$T = C^{-1} \cdot D \cdot E^{-1} = B^{-1} \cdot R$$

$$R = B \cdot C^{-1} \cdot D \cdot E^{-1} \qquad \text{[Equation 1]}$$

In some embodiments, if each coordinate transformation relationship is defined inversely, the equation for obtaining the coordinate transformation relationship R may be as follows.

$$T = E^{-1} \cdot D \cdot C^{-1} = R \cdot B^{-1}$$

$$R = E^{-1} \cdot D \cdot C^{-1} \cdot B \qquad \text{[Equation 2]}$$

The processor may match the coordinate system of the virtual vertebrae measurement image 4030 with the coordinate system of the patient 2020 using the obtained coordinate transformation relationship R. A doctor and/or a robot arm may perform vertebrae surgery according to the estimated vertebrae position along the dorsal surface based on the virtual vertebrae measurement image matched with the body of the patient.

In the process of matching the virtual vertebrae measurement image 4030 with the body of the patient, a change may be made to the virtual vertebrae measurement image. For example, the virtual vertebrae measurement image may be scaled up or down, or the spatial offset of the virtual vertebrae measurement image in the x, y and z directions may be adjusted for accurate matching with the body of the patient.

In one embodiment, the tracking sensor 1020 may continuously track the position and posture information of the reference marker 3010 fixed to the patient during surgery. When a change equal to or greater than a predetermined value is detected in the position or posture of the reference marker 3010, the tracking sensor 1020 may inform the processor of such a change. The processor may determine that the posture of the patient 2020 has changed during the surgery, and may rematch the virtual vertebrae measurement image 4030. The processor may perform the above-described matching process again to rematch the coordinate system of the virtual vertebrae measurement image 4030 with the coordinate system of the patient 2020.

Figure 8:
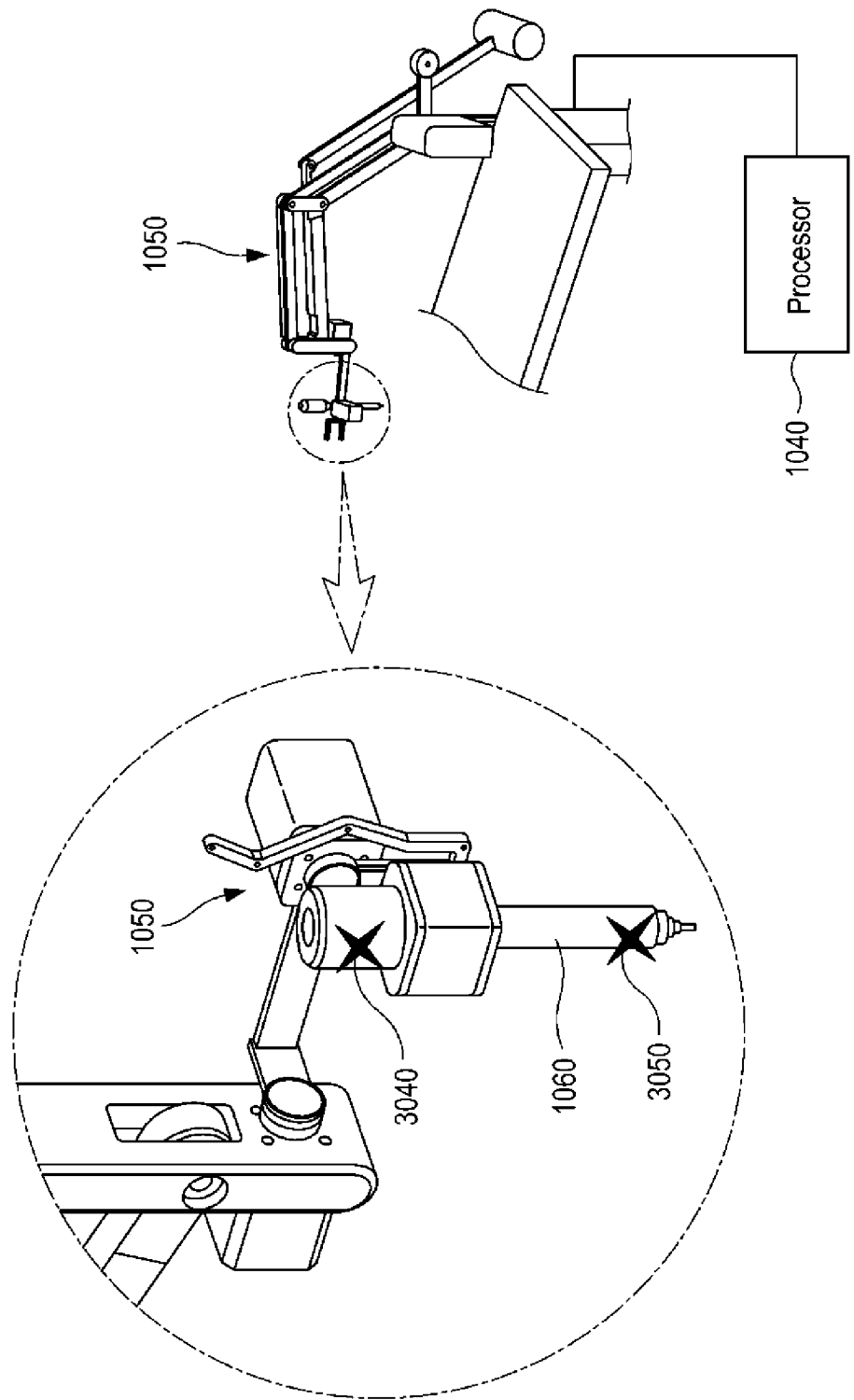
FIG. 8 is a diagram showing a process of controlling a robot arm using a matched virtual vertebrae measurement image according to an embodiment of the present disclosure.

FIG. 8 is a diagram showing a process of controlling a robot arm using the matched virtual vertebrae measurement image according to an embodiment of the present disclosure.

In some embodiments, the image matching device may further include a robot arm 1050. The robot arm 1050 may be positioned alongside the surgery table and may be attached to a movable robot base. Alternatively, the robot arm 1050 may be directly attached to the surgery table. A detachable surgical tool 1060 may be further attached to the distal end of the robot arm 1050.

A marker 3040 may be attached to the robot arm 1050. This marker 3040 may be referred to as a robot arm marker. The tracking sensor may obtain position and posture information of the robot arm marker 3040. Accordingly, position coordinates or posture information of the robot arm 1050 and the surgical tool 1060 may be obtained on the coordinate system of the patient with which the virtual vertebrae measurement image is matched.

A marker 3050 may be further attached to the surgical tool 1060 attached to the distal end of the robot arm 1050. The marker 3050 attached to the surgical tool may be a lightweight or small marker. The tracking sensor may obtain position and posture information of the marker 3050 attached to the surgical tool. Accordingly, position coordinates or posture information of the surgical tool 1060 may be obtained on the coordinate system of the patient with which the virtual vertebrae measurement image is matched.

The processor 1040 may control the robot arm. The processor 1040 may send a signal for controlling the robot arm to the robot arm 1050 to control the position, posture, motion and the like of the robot arm.

In controlling the robot arm, the processor 1040 may use the position and posture information of the robot arm marker 3040 obtained from the tracking sensor and/or the virtual vertebrae measurement image. In this regard, the position information of the robot arm marker 3040 may be spatial position coordinates based on the coordinate system of the patient matched with the coordinate system of the virtual vertebrae measurement image. The posture information of the robot arm marker 3040 may be information about the posture of the robot arm marker 3040 on the coordinate system of the patient. The processor 1040 may transmit a control signal to cause the robot arm to move to a specific position or in a specific posture by using the position and posture information of the robot arm 1050 appearing on the coordinate system of the patient and the estimated vertebrae position appearing in the virtual vertebrae measurement image.

The processor 1040 may also control the posture of the surgical tool by using the position and posture information of the marker received from the tracking sensor. If the position and posture information of the marker 3050 attached to the surgical tool and the position and posture information of the robot arm marker 3040 are used at the same time, it is possible to obtain posture information such as the current inclination degree of the surgical tool 1060 or the like. The processor 1040 may obtain the posture information of the surgical tool and may transmit a control signal to the robot arm 1050 based on this information to control the posture of the surgical tool.

In one embodiment, when a sudden change in the position or posture of the robot arm marker 3040 and/or the marker 3050 attached to the surgical tool is sensed by the tracking sensor, the processor 1040 may transmit a signal to the robot arm 1050 to immediately stop the operation of the robot arm 1050. When there is a sudden change in the position or posture of each marker detected by the tracking sensor, the processor 1040 may transmit a control signal to the robot arm 1050 to stop the robot arm 1050 for the safety of the patient.

FIG. 9 is a diagram showing an image matching method that may be implemented by the image matching device according to an embodiment of the present disclosure.

Although process steps, method steps, algorithms, etc. are illustrated in a sequential order in the flowchart shown in FIG. 9, such processes, methods, and algorithms may be configured to be operated in any suitable order. In other words, the steps in the processes, methods, and algorithms explained in various embodiments of the present disclosure are not necessarily performed in the order described in the present disclosure. Further, even though some steps are explained as being performed non-simultaneously, such steps may be simultaneously performed in another embodiment. Moreover, the illustration of the processes depicted in the figure does not mean that the illustrated processes exclude other changes and modifications thereto, that any of the illustrated processes or the steps thereof is essential for at least one of various embodiments of the present disclosure, and that the illustrated processes are desirable.

The image matching method according to an embodiment of the present disclosure may include: a step (S9010) of obtaining a first dorsal surface scan image of a patient in a first posture; a step (S9020) of obtaining position and posture information of a reference marker and/or position and posture information of a scanner marker; a step (S9030) of generating a virtual first vertebrae measurement image based on a human body correlation model and/or the first dorsal surface scan image; and/or a step (S9040) of matching the virtual first vertebrae measurement image with the patient.

First, the 3D scanner 1010 may obtain a first dorsal surface scan image by three-dimensionally scanning the dorsal surface of the patient supported on the surgery table and kept in a first posture (S9010).

The tracking sensor 1020 may obtain the position and posture information of the reference marker provided on the body of the patient to be subjected to surgery and/or the position and posture information of the scanner marker provided on the 3D scanner (S9020).

The memory 1030 may store a human body correlation model regarding a correlation between the dorsal surface and the vertebrae of the human body. The processor 1040, which is electrically connected to the 3D scanner 1010, the tracking sensor 1020 and/or the memory 1030, may generate a virtual first vertebrae measurement image for estimating the position of the vertebrae of the patient to be subjected to surgery, based on the human body correlation model and/or the first dorsal surface scan image (s9030).

In addition, the processor 1040 may match the coordinate system of the virtual first vertebrae measurement image with the coordinate system of the patient to be subjected to surgery, based on the position and posture information of the reference marker and/or the position and posture information of the scanner marker (S9040).

In one embodiment, the processor 1040 may extract the dorsal surface information of the patient in the first posture to be subjected to surgery from the first dorsal surface scan image. Furthermore, the processor 1040 may obtain the vertebrae position information of the patient in the first posture to be subjected to surgery, based on the human body correlation model and/or the dorsal surface information. In addition, the processor 1040 may generate a virtual first vertebrae measurement image based on the obtained vertebrae position information.

In one embodiment, the human body correlation model may be a first correlation model that is generated by using the correlation between a second dorsal surface scan image obtained by three-dimensionally scanning the dorsal surface in a second posture of the patient to be subjected to surgery and a second vertebrae measurement image obtained by capturing an image of the vertebrae in the second posture of the patient to be subjected to surgery. The first correlation model may be the aforementioned patient-specific human body correlation model.

In one embodiment, the human body correlation model may be a second correlation model that is generated by correcting the first correlation model using a correlation between a third dorsal surface scan image obtained by three-dimensionally scanning the dorsal surface of at least one patient selected from a group of different patients and a third vertebrae measurement image obtained by capturing an image of the vertebrae of the at least one patient. The second correlation model may be the aforementioned database-based human body correlation model.

In one embodiment, the vertebrae image camera of the image matching device may obtain a fourth vertebrae measurement image by capturing an image of the vertebrae of the patient in the first posture to be subjected to surgery. The processor 1040 may correct the human body correlation model by using the correlation between the fourth vertebrae measurement image and the first dorsal surface scan image. This correction may be a correction of the above-described human body correlation model for the intra-operative posture. The processor 1040 may generate a virtual first vertebrae measurement image by using the corrected human body correlation model.

In one embodiment, the processor 1040 may repeatedly perform the correction of the human body correlation model based on the fourth vertebrae measurement image a predetermined number of times.

In one embodiment, the tracking sensor 1020 may obtain position and posture information of a robot arm marker provided on a robot arm. In this regard, the image matching device may further include a robot arm having a surgical tool attached to the distal end thereof. In this case, the processor 1040 may control the robot arm based on the position and posture of the robot arm marker appearing on the coordinate system of the patient matched with the coordinate system of the virtual first vertebrae measurement image.

In one embodiment, the processor 1040 may obtain a third coordinate transformation relationship between the virtual first vertebrae measurement image and the position and posture information of the reference marker, based on the position and posture information of the reference marker, the position and posture information of the scanner marker, a first coordinate transformation relationship between the position and posture information of the scanner marker and the first dorsal surface scan image, and/or a second coordinate transformation relationship between the first dorsal surface scan image and the virtual first vertebrae measurement image. In addition, the processor 1040 may match the coordinate system of the virtual first vertebrae measurement image with the coordinate system of the patient based on the third coordinate transformation relationship.

In one embodiment, the second vertebrae measurement image, the third vertebrae measurement image and/or the fourth vertebrae measurement image may be one of the CTA image, the MRI image and the CT image described above.

While the foregoing methods have been described with respect to particular embodiments, these methods may also be implemented as computer-readable codes on a computer-readable recording medium. The computer-readable recoding medium includes any kind of data storage devices that can be read by a computer system. Examples of the computer-readable recording medium include ROM, RAM, CD-ROM, magnetic tape, floppy disk, optical data storage device and the like. Also, the computer-readable recoding medium can be distributed on computer systems which are connected through a network so that the computer-readable codes can be stored and executed in a distributed manner. Further, the functional programs, codes and code segments for implementing the foregoing embodiments can easily be inferred by programmers in the art to which the present disclosure pertains.

Although the technical spirit of the present disclosure has been described by the examples described in some embodiments and illustrated in the accompanying drawings, it should be noted that various substitutions, modifications, and changes can be made without departing from the scope of the present disclosure which can be understood by those skilled in the art to which the present disclosure pertains. In addition, it should be noted that such substitutions, modifications and changes are intended to fall within the scope of the appended claims.

What is claimed is:

1. An image matching device, comprising:
 a 3D scanner configured to three-dimensionally scan a dorsal surface of a patient supported on a surgery table in a first posture to obtain a first dorsal surface scan image;
 a tracking sensor configured to obtain position and posture information of a reference marker provided on a body of the patient and position and posture information of a scanner marker provided on the 3D scanner;
 a memory configured to store a human body correlation model on a correlation between the dorsal surface and a vertebrae of the patient; and
 a processor electrically connected to the 3D scanner, the tracking sensor and the memory, the processor configured to:
 generate a virtual first vertebrae measurement image for estimation of a position of the vertebrae of the patient based on the human body correlation model and the first dorsal surface scan image; and
 match a coordinate system of the virtual first vertebrae measurement image with a coordinate system of the patient based on the position and posture information of the reference marker and the position and posture information of the scanner marker.

2. The device of claim 1, wherein the processor is further configured to:
extract dorsal surface information of the patient in the first posture from the first dorsal surface scan image;
obtain vertebrae position information of the patient in the first posture based on the human body correlation model and the dorsal surface information; and
generate the virtual first vertebrae measurement image based on the vertebrae position information.

3. The device of claim 1, wherein the human body correlation model is a first correlation model that is generated by using a correlation between a second dorsal surface scan image obtained by three-dimensionally scanning the dorsal surface of the patient in a second posture and a second vertebrae measurement image obtained by capturing an image of the vertebrae of the patient in the second posture.

4. The device of claim 3, wherein the human body correlation model is a second correlation model that is generated by correcting the first correlation model using a correlation between a third dorsal surface scan image obtained by three-dimensionally scanning the dorsal surface of at least one patient selected from a group of a plurality of different patients and a third vertebrae measurement image obtained by capturing an image of a vertebrae of the at least one patient.

5. The device of claim 4, further comprising:
a vertebrae image camera configured to capture an image of the vertebrae of the patient in the first posture to obtain a fourth vertebrae measurement image,
wherein the processor is further configured to:
correct the human body correlation model using a correlation between the fourth vertebrae measurement image and the first dorsal surface scan image; and
generate the virtual first vertebrae measurement image using the corrected human body correlation model.

6. The device of claim 5, wherein the processor is further configured to:
repeatedly perform, a predetermined number of times, a correction of the human body correlation model based on the fourth vertebrae measurement image.

7. The device of claim 1, further comprising:
a robot arm having a distal end to which a surgical tool is attached,
wherein the tracking sensor obtains position and posture information of a robot arm marker provided on the robot arm, and the processor controls the robot arm based on the position and posture information of the robot arm marker appearing on the coordinate system of the patient matched with the coordinate system of the virtual first vertebrae measurement image.

8. The device of claim 1, wherein the processor is further configured to:
obtain a third coordinate transformation relationship between the virtual first vertebrae measurement image and the position and posture information of the reference marker, based on the position and posture information of the reference marker, the position and posture information of the scanner marker, a first coordinate transformation relationship between the position and posture information of the scanner marker and the first dorsal surface scan image and a second coordinate transformation relationship between the first dorsal surface scan image and the virtual first vertebrae measurement image; and
match the coordinate system of the virtual first vertebrae measurement image with the coordinate system of the patient based on the third coordinate transformation relationship.

9. The device of claim 5, wherein each of the second vertebrae measurement image, the third vertebrae measurement image and the fourth vertebrae measurement image is one of a Computed Tomography Angiograph (CTA) image, a Magnetic Resonance Imaging (MRI) image and a Computed Tomography (CT) image.

10. An image matching method, comprising:
obtaining, by a 3D scanner, a first dorsal surface scan image by three-dimensionally scanning a dorsal surface of a patient supported on a surgery table in a first posture;
obtaining position and posture information of a reference marker provided on a body of the patient and position and posture information of a scanner marker provided on the 3D scanner;
generating a virtual first vertebrae measurement image for estimation of a position of a vertebrae of the patient based on a human body correlation model on a correlation between the dorsal surface and the vertebrae of the patient and the first dorsal surface scan image; and
matching a coordinate system of the virtual first vertebrae measurement image with a coordinate system of the patient based on the position and posture information of the reference marker and the position and posture information of the scanner marker.

11. The method of claim 10, wherein the generating the virtual first vertebrae measurement image includes:
extracting dorsal surface information of the patient in the first posture from the first dorsal surface scan image;
obtaining vertebrae position information of the patient in the first posture based on the human body correlation model and the dorsal surface information; and
generating the virtual first vertebrae measurement image based on the vertebrae position information.

12. The method of claim 10, wherein the human body correlation model is a first correlation model that is generated by using a correlation between a second dorsal surface scan image obtained by three-dimensionally scanning the dorsal surface of the patient in a second posture and a second vertebrae measurement image obtained by capturing an image of the vertebrae of the patient in the second posture.

13. The method of claim 12, wherein the human body correlation model is a second correlation model that is generated by correcting the first correlation model using a correlation between a third dorsal surface scan image obtained by three-dimensionally scanning the dorsal surface of at least one patient selected from a group of different patients and a third vertebrae measurement image obtained by capturing an image of a vertebrae of the at least one patient.

14. The method of claim 13, further comprising:
obtaining a fourth vertebrae measurement image by capturing an image of the vertebrae of the patient in the first posture; and
correcting the human body correlation model using a correlation between the fourth vertebrae measurement image and the first dorsal surface scan image,
wherein the generating the virtual first vertebrae measurement image includes generating the virtual first vertebrae measurement image using the corrected human body correlation model.

15. The method of claim 14, wherein the correcting the human body correlation model is repeatedly performed a predetermined number of times.

16. The method of claim 10, further comprising:
obtaining position and posture information of a robot arm marker provided on a robot arm having a distal end to which a surgical tool is attached; and
controlling the robot arm based on the position and posture information of the robot arm marker appearing on the coordinate system of the patient matched with the coordinate system of the virtual first vertebrae measurement image.

17. The method of claim 10, wherein the matching the coordinate system of the virtual first vertebrae measurement image with the coordinate system of the patient includes:
obtaining a third coordinate transformation relationship between the virtual first vertebrae measurement image and the position and posture information of the reference marker, based on the position and posture information of the reference marker, the position and posture information of the scanner marker, a first coordinate transformation relationship between the position and posture information of the scanner marker and the first dorsal surface scan image and a second coordinate transformation relationship between the first dorsal surface scan image and the virtual first vertebrae measurement image; and
matching the coordinate system of the virtual first vertebrae measurement image with the coordinate system of the patient based on the third coordinate transformation relationship.

18. The method of claim 14, wherein each of the second vertebrae measurement image, the third vertebrae measurement image and the fourth vertebrae measurement image is one of a Computed Tomography Angiograph (CTA) image, a Magnetic Resonance Imaging (MRI) image and a Computed Tomography (CT) image.

19. A non-transitory computer-readable recording medium storing a program to be executed on a computer, the program including executable commands for, when executed by a processor, causing the processor to perform:
obtaining a first dorsal surface scan image by causing a 3D scanner to three-dimensionally scan a dorsal surface of a patient supported on a surgery table in a first posture;
obtaining position and posture information of a reference marker provided on a body of the patient and position and posture information of a scanner marker provided on the 3D scanner;
generating a virtual first vertebrae measurement image for estimation of a position of a vertebrae of the patient based on a human body correlation model on a correlation between the dorsal surface and the vertebrae of the patient and the first dorsal surface scan image; and
matching a coordinate system of the virtual first vertebrae measurement image with a coordinate system of the patient based on the position and posture information of the reference marker and the position and posture information of the scanner marker.

20. The recording medium of claim 19, wherein the human body correlation model is a first correlation model that is generated by using a correlation between a second dorsal surface scan image obtained by three-dimensionally scanning the dorsal surface of the patient in a second posture and a second vertebrae measurement image obtained by capturing an image of the vertebrae of the patient in the second posture.

* * * * *